(12) United States Patent
Boucher et al.

(10) Patent No.: US 7,938,835 B2
(45) Date of Patent: May 10, 2011

(54) SYSTEMS AND METHODS FOR TREATING VERTEBRAL BODIES

(75) Inventors: Ryan P Boucher, San Francisco, CA (US); Mark A Reiley, Piedmont, CA (US); Robert M Scribner, Los Altos, CA (US); Michael L Reo, Redwood City, CA (US)

(73) Assignee: Kyphon SARL, Neuchatel (CH)

( * ) Notice: Subject to any disclaimer, the term of this patent is extended or adjusted under 35 U.S.C. 154(b) by 647 days.

(21) Appl. No.: 10/842,076

(22) Filed: May 10, 2004

(65) Prior Publication Data
US 2004/0210231 A1    Oct. 21, 2004

Related U.S. Application Data

(60) Division of application No. 10/346,618, filed on Jan. 17, 2003, now abandoned, which is a division of application No. 09/597,646, filed on Jun. 20, 2000, now Pat. No. 6,716,216, which is a continuation-in-part of application No. 09/134,323, filed on Aug. 14, 1998, now Pat. No. 6,241,734.

(51) Int. Cl.
*A61B 17/58* (2006.01)
(52) U.S. Cl. .......................................... 606/93; 606/92
(58) Field of Classification Search ............... 606/92–94
See application file for complete search history.

(56) References Cited

U.S. PATENT DOCUMENTS

| | | | |
|---|---|---|---|
| 3,833,003 A * | 9/1974 | Taricco | 604/509 |
| 4,005,527 A | 2/1977 | Wilson et al. | |
| 4,083,369 A | 4/1978 | Sinnreich | |
| 4,299,226 A | 11/1981 | Banka | |
| 4,313,434 A | 2/1982 | Segal | |
| 4,327,736 A | 5/1982 | Inoue | |
| 4,705,510 A | 11/1987 | Rosenberg | |
| 4,919,153 A | 4/1990 | Chin | |
| 4,969,888 A * | 11/1990 | Scholten et al. | 606/94 |
| 5,013,318 A | 5/1991 | Spranza, III | |
| 5,037,437 A * | 8/1991 | Matsen, III | 128/898 |
| 5,090,957 A | 2/1992 | Moutafis et al. | |
| 5,108,404 A | 4/1992 | Scholten et al. | |
| 5,116,305 A | 5/1992 | Milder et al. | |
| 5,171,248 A | 12/1992 | Ellis | |
| 5,254,091 A | 10/1993 | Aliahmad | |

(Continued)

FOREIGN PATENT DOCUMENTS
EP    0 890 341    1/1999
(Continued)

*Primary Examiner* — Eduardo C Robert
*Assistant Examiner* — Julianna N Harvey
(74) *Attorney, Agent, or Firm* — Haynes and Boone, LLP

(57) ABSTRACT

A system for treating a vertebral body comprises a cannula leading into a vertebral body and a cavity creating device. The cavity creating device comprises a shaft having a distal end portion sized to extend through the cannula, an expandable body that undergoes expansion between a collapsed condition and an expanded condition to form a cavity in the vertebral body, and a tubular fluid transport member to convey fluid through the distal region of the expandable body and into the cavity. The system further comprises a device coupled to the shaft to change the expandable body between the collapsed condition to the expanded condition. The system further comprises a source of fluid coupled to the tubular fluid transport member to convey fluid through the distal region of the expandable body and into the cavity. The system further includes a device to convey a filling material into the cavity.

9 Claims, 31 Drawing Sheets

U.S. PATENT DOCUMENTS

| | | |
|---|---|---|
| 5,385,566 A | 1/1995 | Ullmark |
| 5,439,447 A | 8/1995 | Miraki |
| 5,468,245 A | 11/1995 | Vargas, III |
| 5,514,137 A | 5/1996 | Coutts |
| 5,658,310 A | 8/1997 | Berger |
| 5,704,909 A * | 1/1998 | Morrey et al. ............... 604/26 |
| 5,749,888 A | 5/1998 | Yock |
| 5,849,014 A * | 12/1998 | Mastrorio et al. ............ 606/94 |
| 5,972,015 A * | 10/1999 | Scribner et al. ............. 606/192 |
| 5,989,260 A | 11/1999 | Yao |
| 5,997,581 A | 12/1999 | Khalili |
| 6,017,348 A | 1/2000 | Hart et al. |
| 6,146,358 A | 11/2000 | Rowe |
| 6,241,734 B1 | 6/2001 | Scribner et al. |
| 6,423,083 B2 | 7/2002 | Reiley et al. |
| 6,852,095 B1 * | 2/2005 | Ray ........................... 604/93.01 |

FOREIGN PATENT DOCUMENTS

| | | |
|---|---|---|
| JP | 8038618 | 2/1996 |
| WO | WO 98/56301 | 1/1998 |
| WO | 9856301 | 12/1998 |
| WO | WO 99/51149 | 1/1999 |
| WO | WO 99/49819 | 10/1999 |
| WO | WO 99/62416 | 12/1999 |
| WO | WO 00/67650 | 11/2000 |

* cited by examiner

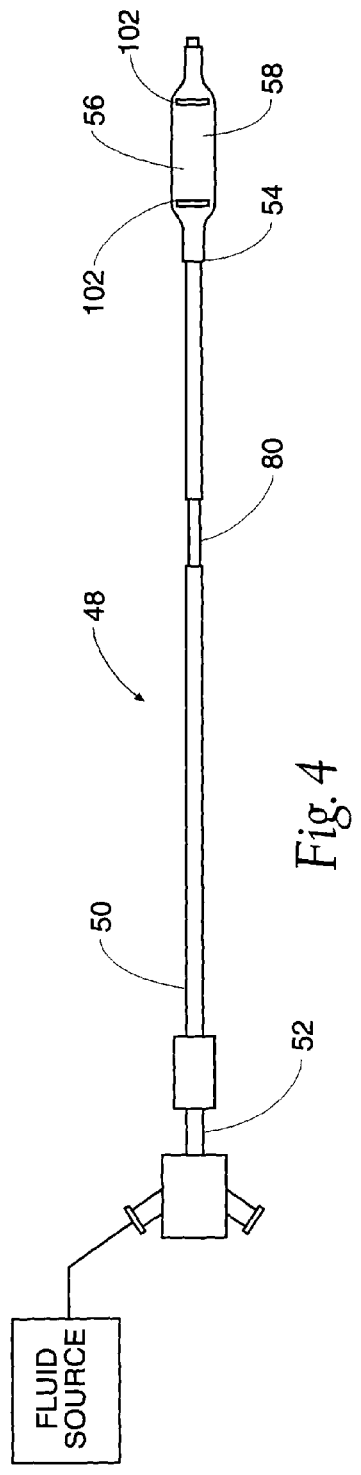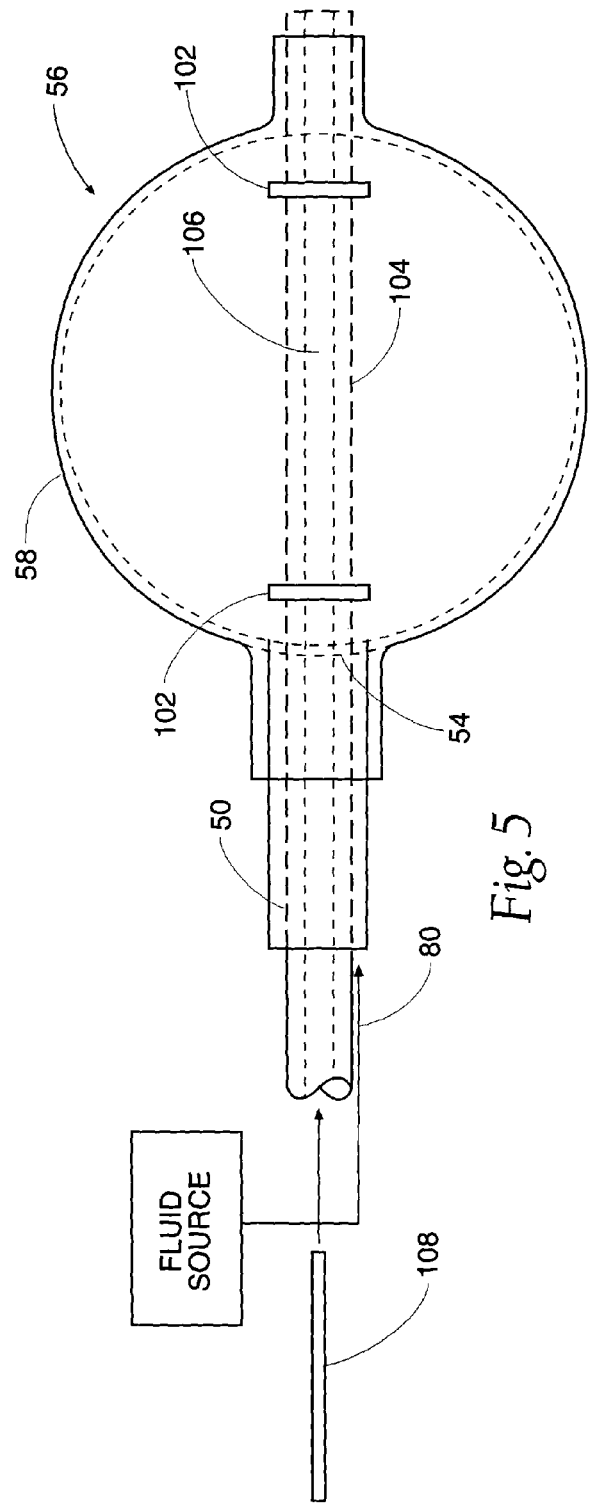

SYSTEMS AND METHODS FOR TREATING VERTEBRAL BODIES

RELATED APPLICATIONS

This application is a divisional of co-pending U.S. application Ser. No. 10/346,618, filed Jan. 17, 2003, now abandoned which is a divisional of U.S. application Ser. No. 09/597,646 filed Jun. 20, 2000, now U.S. Pat. No. 6,716,216, which is a continuation-in-part of application Ser. No. 09/134,323, filed Aug. 14, 1998, now U.S. Pat. No. 6,241,734.

FIELD OF THE INVENTION

The invention generally relates to the treatment of bone conditions in humans and other animals.

BACKGROUND OF THE INVENTION

The deployment of expandable structures, generically called "balloons," into cancellous bone is known. For example, U.S. Pat. Nos. 4,969,888 and 5,108,404 disclose apparatus and methods using expandable structures in cancellous bone for the fixation of fractures or other osteoporotic and non-osteoporotic conditions of human and animal bones.

SUMMARY OF THE INVENTION

The invention provides systems and methods for treating bone.

According to one aspect of the invention, the systems and methods treat at least two vertebral bodies in a spinal column. The systems and methods make use of first and second tool assemblies operable to treat an interior region of, respectively, a first vertebral body and a second vertebral body in the spinal column. The systems and methods provide directions for operating the first and second tool assemblies to treat the first and second vertebral bodies, at least for a portion of time, concurrently.

According to another aspect of the invention, the systems and methods employ a device for compacting cancellous bone. The device comprises a wall adapted to be inserted into bone and undergo expansion in cancellous bone to compact cancellous bone. The systems and methods include a cortical bone plugging material inserted into the bone either before or after expansion of the device.

According to another aspect of the invention, the systems and methods include an instrument introducer defining an access passage into cancellous bone through cortical bone. The systems and methods also include an instrument including a distal body portion having a dimension sized for advancement through the access passage to penetrate cancellous bone. In one embodiment, the instrument includes a proximal stop having a dimension greater than the access passage and having a location to prevent penetration of the distal body portion beyond a selected depth in cancellous bone. In another embodiment, the distal body region includes a blunt terminus to tactilely indicate contact with cortical bone without breaching the cortical bone.

According to another aspect of the invention, the systems and methods use an instrument introducer defining an access passage into cancellous bone through cortical bone. A gripping device rests on an exterior skin surface and engages the instrument introducer to maintain the instrument introducer in a desired orientation.

According to another aspect of the invention, the systems and methods include a device adapted to be inserted into bone in a collapsed condition and thereafter expanded to form a cavity in cancellous bone. The systems and methods employ a fluid transport passage to convey fluid from a source into the cavity to resist formation of a vacuum inside the cavity as the device is returned to the collapsed condition and withdrawn from bone.

According to another aspect of the invention, the systems and methods include a device adapted to be inserted into bone and undergo expansion in cancellous bone. A transport passage conveys an expansion medium into the device. The expansion medium includes an amount of material to enable visualization of the expansion. The systems and methods include an exchanger assembly communicating with the transport passage and operating to reduce the amount of material present in the expansion medium within the device.

Another aspect of the invention provides systems and methods for forming an opening in cortical bone. In one embodiment, the systems and methods employ a support body including a flexible shaft portion. A cortical bone cutting element is carried on the flexible shaft portion. The element operates to form an opening in cortical body in response to application of force. In another embodiment, a cortical bone cutting element is carried on a support body to form an opening into the bone. An expandable structure also carried on the support body and adapted to be inserted through the opening and expanded to form a cavity in cancellous bone.

Features and advantages of the various aspects of the invention are set forth in the following Description and Drawings, as well as in the appended Claims.

BRIEF DESCRIPTION OF THE DRAWINGS

FIG. 4 is a plan view of a tool which carries at its distal end an expandable structure, which, in use, compresses cancellous bone, the structure being shown in a collapsed condition;

FIG. 5 is enlarged side view of the expandable structure carried by the tool shown in FIG. 4;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification describes new systems and methods to treat bones using expandable bodies. The use of expandable bodies to treat bones is generally disclosed in U.S. Pat. Nos. 4,969,888 and 5,108,404, which are incorporated herein by reference. Improvements in this regard are disclosed in U.S. patent application, Ser. No. 08/188,224, filed Jan. 26, 1994; U.S. patent application Ser. No. 08/485,394, filed Jun. 7, 1995; and U.S. patent application Ser. No. 08/659,678, filed Jun. 5, 1996, which are each incorporated herein by reference.

The new systems and methods will be described with regard to the treatment of vertebral bodies. It should be appreciated, however, the systems and methods so described are not limited in their application to vertebrae. The systems and methods are applicable to the treatment of diverse bone types, including, but not limited to, such bones as the radius, the humerus, the femur, the tibia, or the calcanus.

I. Vertebral Bodies

Figure 1:
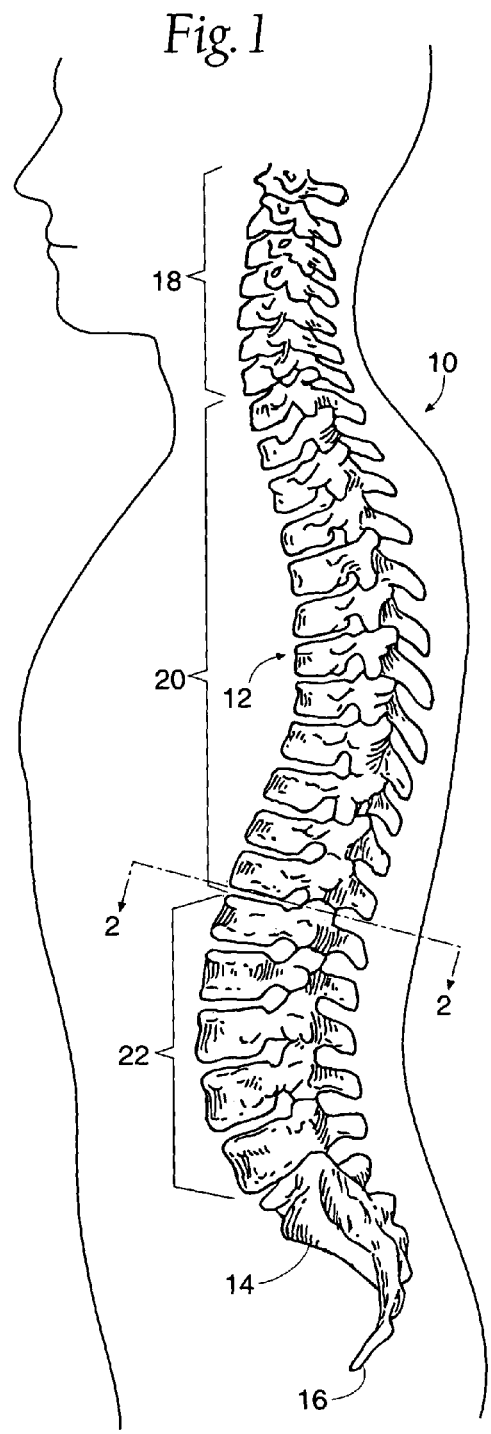
FIG. 1 is a lateral view of a human spinal column.

As FIG. 1 shows, the spinal column 10 comprises a number of uniquely shaped bones, called the vertebrae 12, a sacrum 14, and a coccyx 16 (also called the tail bone). The number of vertebrae 12 that make up the spinal column 10 depends upon the species of animal. In a human (which FIG. 1 shows), there are twenty-four vertebrae 12, comprising seven cervical, vertebrae 18, twelve thoracic vertebrae 20, and five lumbar vertebrae 22.

When viewed from the side, as FIG. 1 shows, the spinal column 10 forms an S-shaped curve. The curve serves to support the head, which is heavy. In four-footed animals, the curve of the spine is simpler.

Figure 2:
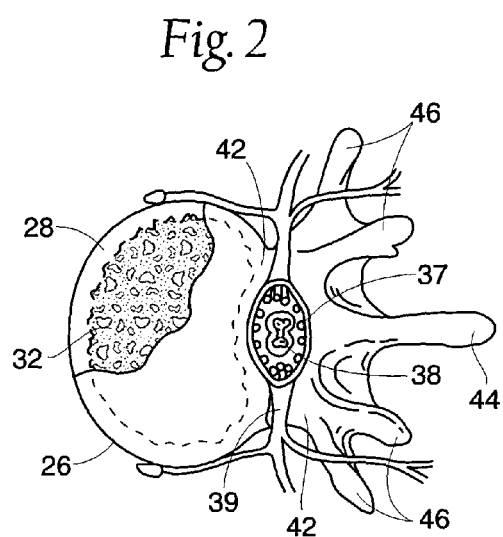
FIG. 2 is a representative coronal view, with portions broken away and in section, of a human vertebral body, taken generally along line 2-2 in FIG. 1.
Figure 3:
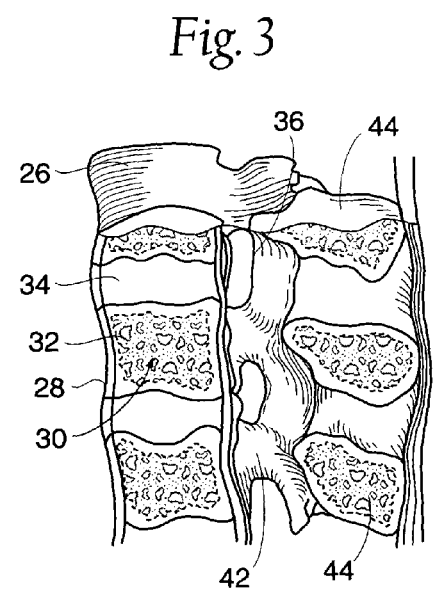
FIG. 3 is a lateral view, with portions broken away and in section, of several vertebral bodies, which are part of the spinal column shown in FIG. 1.

As FIGS. 1 to 3 show, each vertebra 12 includes a vertebral body 26, which extends on the anterior (i.e., front or chest) side of the vertebra 12. As FIGS. 1 to 3 show, the vertebral body 26 is in the shape of an oval disk. As FIGS. 2 and 3 show, the vertebral body 26 includes an exterior formed from compact cortical bone 28. The cortical bone 28 encloses an interior volume 30 of reticulated cancellous, or spongy, bone 32 (also called medullary bone or trabecular bone). A "cushion," called an intervertebral disk 34, is located between the vertebral bodies 26.

An opening, called the vertebral foramen 36, is located on the posterior (i.e., back) side of each vertebra 12. The spinal ganglion 39 pass through the foramen 36. The spinal cord 38 passes through the spinal canal 37.

The vertebral arch 40 surrounds the spinal canal 37. The pedicle 42 of the vertebral arch 40 adjoins the vertebral body 26. The spinous process 44 extends from the posterior of the vertebral arch 40, as do the left and right transverse processes 46.

II. Treatment of Vertebral Bodies

A. Lateral Access

Access to a vertebral body can be accomplished from many different directions, depending upon the targeted location within the vertebral body, the intervening anatomy, and the desired complexity of the procedure. For example, access can also be obtained through a pedicle 42 (transpedicular), outside of a pedicle (extrapedicular), along either side of the vertebral body (posterolateral), laterally or anteriorly. In addition, such approaches can be used with a closed, minimally invasive procedure or with an open procedure.

FIG. 4 shows a tool 48 for preventing or treating compression fracture or collapse of a vertebral body using an expandable body.

The tool 48 includes a catheter tube 50 having a proximal and a distal end, respectively 52 and 54. The distal end 54 carries a structure 56 having an expandable exterior wall 58. FIG. 4 shows the structure 56 with the wall 58 in a collapsed geometry. FIG. 5 shows the structure 56 in an expanded geometry.

Figure 6:
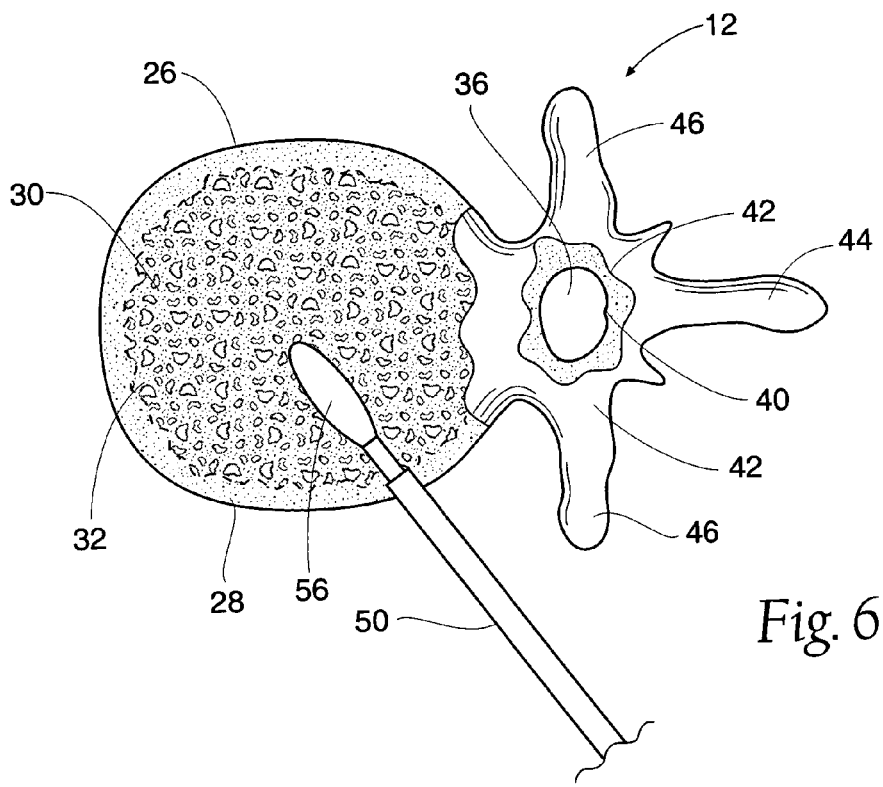
FIG. 6 is a coronal view of the vertebral body shown in FIG. 2, with a single tool shown in FIGS. 4 and 5 deployed through a lateral access in a collapsed condition.

The collapsed geometry permits insertion of the structure 56 into the interior volume 30 of a targeted vertebral body 26, as FIG. 6 shows. The structure 56 can be introduced into the interior volume 30 in various ways. FIG. 6 shows the insertion of the structure 56 through a single lateral access, which extends through a lateral side of the vertebral body 12.

Lateral access is indicated, for example, if a compression fracture has collapsed the vertebral body 26 below the plane of the pedicle 42, or for other reasons based upon the preference of the physician. Lateral access can be performed either with a closed, minimally invasive procedure or with an open procedure. Of course, depending upon the intervening anatomy, well known in the art, lateral access may not be the optimal access path for treatment of vertebrae at all levels of the spine.

Figure 7:
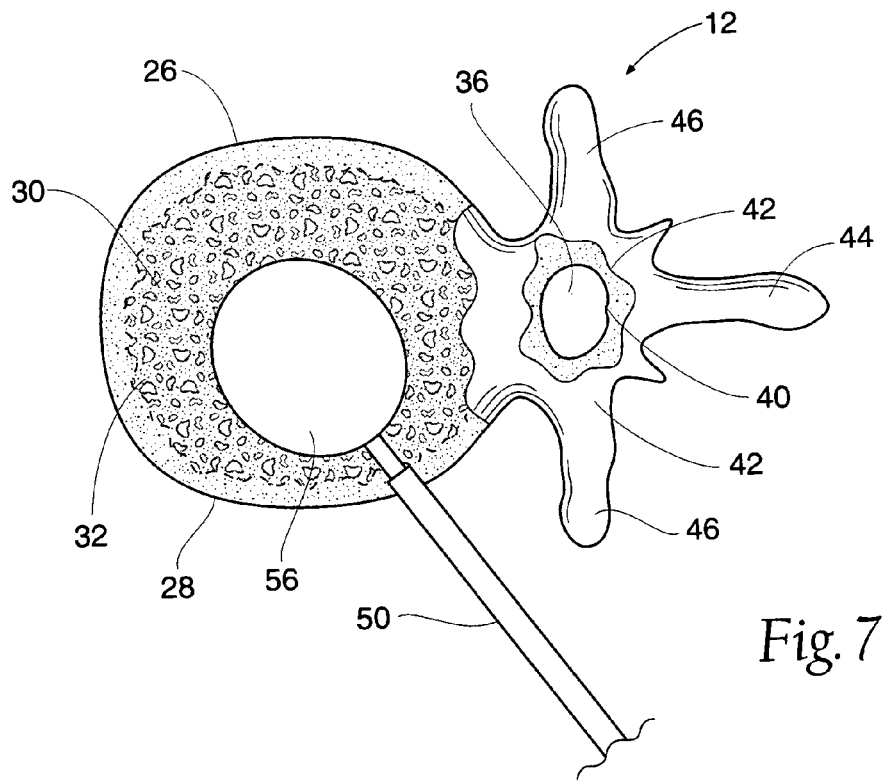
FIG. 7 is a coronal view of the vertebral body and tool shown in FIG. 6, with the tool in an expanded condition to compress cancellous bone and form a cavity.

The catheter tube 50 includes an interior lumen 80 (see FIG. 4). The lumen 80 is coupled at the proximal end of the catheter tube 50 to a pressurized source of fluid, e.g., saline. A syringe containing the fluid can comprise the pressure source. The lumen 80 conveys the fluid into the structure 56 under pressure. As a result, the wall 58 expands, as FIGS. 5 and 7 show.

The fluid is preferably rendered radiopaque, to facilitate visualization as it enters the structure 56. For example, Renografin™ can be used for this purpose. Because the fluid is radiopaque, expansion of the structure 56 can be monitored fluoroscopically or under CT visualization. Using real time MRI, the structure 56 may be filled with sterile water, saline solution, or sugar solution, free of a radiopaque material. If desired, other types of visualization could be used, with the tool 48 carrying compatible reference markers. Alternatively, the structure could incorporate a radiopaque material within the material of the structure, or the structure could be painted or "dusted" with a radiopaque material.

Expansion of the wall 58 enlarges the structure 56, desirably compacting cancellous bone 32 within the interior volume 30 (see FIG. 7) and/or causing desired displacement of cortical bone. The compaction of cancellous bone 32 forms a cavity 60 in the interior volume 30 of the vertebral body 26 (see FIG. 8). As will be described later, a filling material 62 can be safely and easily introduced into the cavity 60 which the compacted cancellous bone 32 forms. In one embodiment, expansion of the structure 56 desirably forms a region of compacted cancellous bone which substantially surrounds the cavity 60. This region desirably comprises a barrier which limits leakage of the filling material 62 outside the vertebral body 26. In an alternate embodiment, the expansion of the structure 56 desirably presses cancellous bone 32 into small fractures which may be present in cortical bone, thereby reducing the possibility of the filling material 62 exiting through the cortical wall. In another alternative embodiment, the expansion of the structure 56 desirably flattens veins in the vertebral body that pass through the cortical wall (e.g., the basivertebral vein), resulting in less opportunity for filling material 62 to extravazate outside the vertebral body through the venous structure in the cortical wall. Alternatively, expansion of the structure 56 will compress less dense and/or weaker regions of the cancellous bone, which desirably increases the average density and/or overall strength of the remaining cancellous bone.

The compaction of cancellous bone by the structure 56 can also exert interior force upon cortical bone. Alternatively, the structure 56 can directly contact the cortical bone, such that expansion and/or manipulation of the structure will cause displacement of the cortical bone. Expansion of the structure 56 within the vertebral body 26 thereby makes it possible to elevate or push broken and compressed bone back to or near its original prefracture position.

Figure 8:
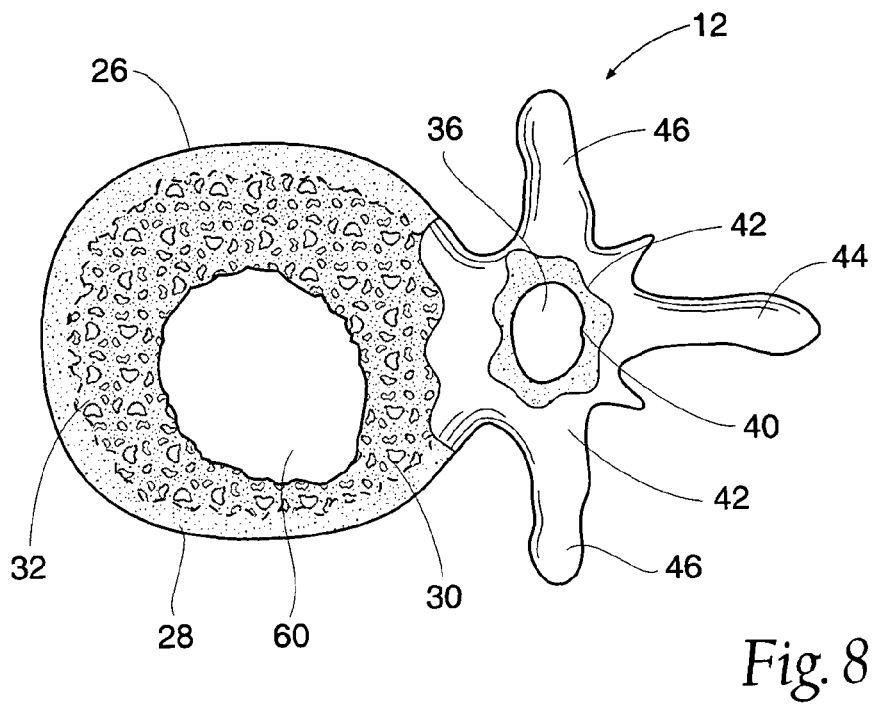
FIG. 8 is a coronal view of the vertebral body shown in FIGS. 6 and 7, with the tool removed after formation of the cavity.

The structure 56 is preferably left inflated within the vertebral body 26 for an appropriate waiting period, for example, three to five minutes, to allow some coagulation inside the vertebral body 26 to occur. After the appropriate waiting period, the physician collapses and removes the structure 56. As FIG. 8 shows, upon removal of the structure 56, the formed cavity 60 remains in the interior volume 30.

Figure 9A:
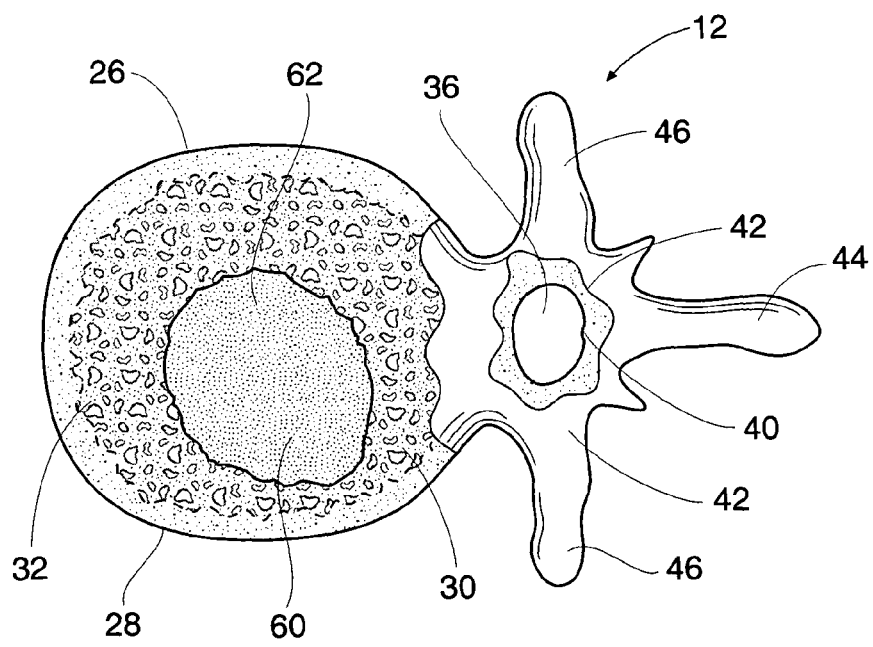
FIG. 9A is a coronal view of the vertebral body shown in FIG. 8, with the cavity filled with a material that strengthens the vertebral body.
Figure 9B:
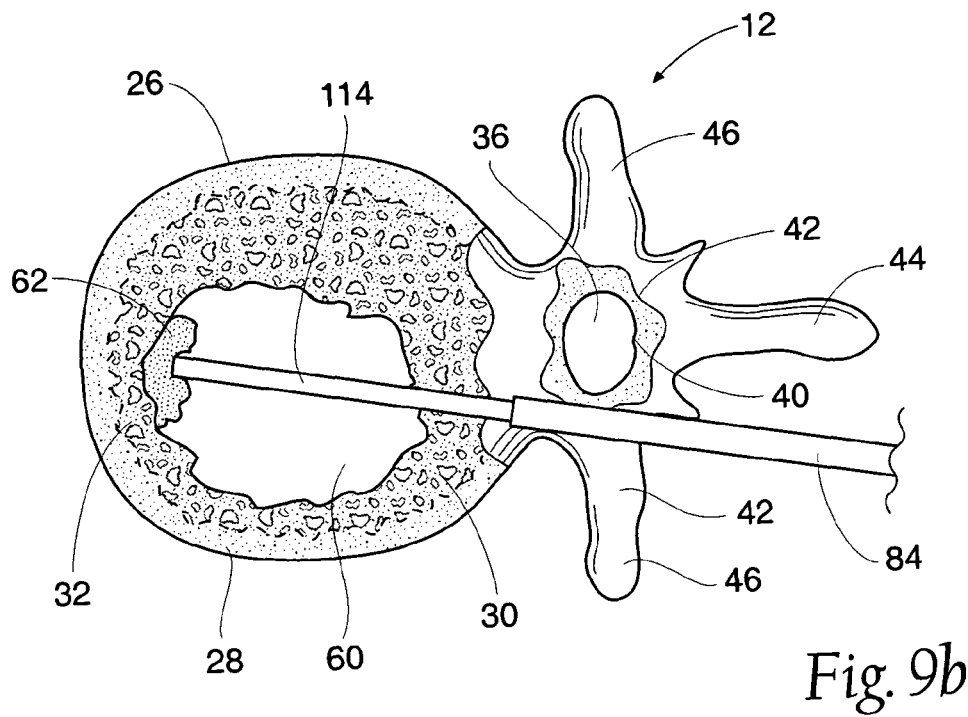
FIG. 9B depicts an alternate method of filling a cavity within a vertebral body.
Figure 9C:
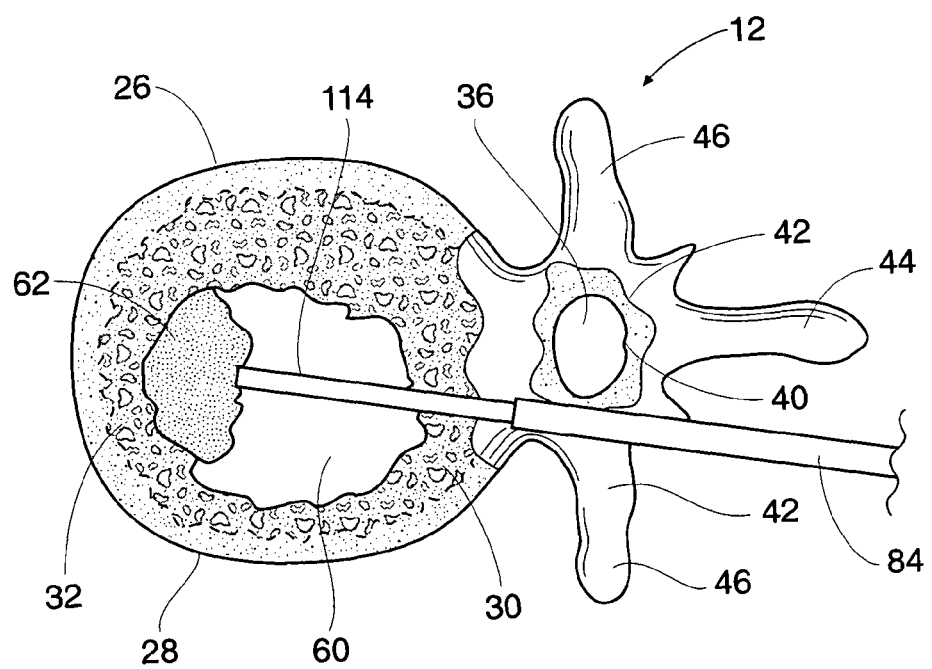
FIG. 9C depicts the vertebral body of FIG. 9B, wherein the cavity is approximately half-filled with material.
Figure 9D:
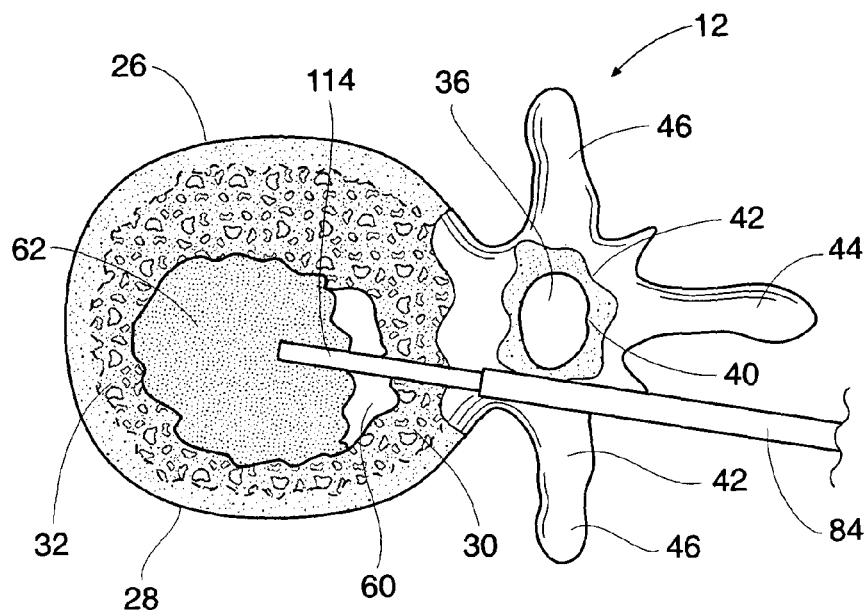
FIG. 9D depicts the vertebral body of FIG. 9B, wherein the cavity is substantially filled with material.

As FIGS. 9B, 9C, and 9D show, the physician next introduces a filling material 62 into the formed cavity 60 using an appropriate nozzle 114 (as will be described in greater detail later). The filling material 62 (which FIG. 9A shows after its introduction into the cavity 60) can comprise a material that resists torsional, tensile, shear and/or compressive forces within the cavity 60, thereby providing renewed interior structural support for the cortical bone 28. For example, the material 62 can comprise a flowable material, such as bone cement, allograft tissue, autograft tissue, or hydroxyapatite, synthetic bone substitute, which is introduced into the cavity 60 and which, in time, sets to a generally hardened condition. The material 62 can also comprise a compression-resistant material, such as rubber, polyurethane, cyanoacrylate, or silicone rubber, which is inserted into the cavity 60. The material 62 can also comprise a semi-solid slurry material (e.g., a bone slurry in a saline base), which is either contained within a porous fabric structure located in the cavity 60 or injected directly into the cavity 60, to resist compressive forces within the cavity 60. Alternatively, the material 62 could comprise stents, reinforcing bar (Re-Bar) or other types of internal support structures, which desirably resist compressive, tensile, torsional and/or shear forces acting on the bone and/or filler material.

The filling material 62 may also comprise a medication, or a combination of medication and a compression-resistant material, as described above.

Alternatively, the filling material 62 can comprise a bone filling material which does not withstand compressive, tensile, torsional and/or shear forces within the cavity. For example, where the patient is not expected to experience significant forces within the spine immediately after surgery, such as where the patient is confined to bed rest or wears a brace, the filling material 62 need not be able to immediately bear load. Rather, the filling material 62 could provide a scaffold for bone growth, or could comprise a material which facilitates, or accelerates bone growth, allowing the bone to heal over a period of time. As another alternative, the filling material could comprise a resorbable or partially-resorbable source of organic or inorganic material for treatment of various bone or non-bone-related disorders including, but not limited to, osteoporosis, cancer, degenerative disk disease, heart disease, acquired immune deficiency syndrome (AIDS) or diabetes. In this way, the cavity and/or filler material could comprise a source of material for treatment of disorders located outside the treated bone.

In an alternative embodiment, following expansion, the expandable structure 56 can be left in the cavity 60. In this arrangement, flowable filling material 62 is conveyed into the structure 56, which serves to contain the material 62. The structure 56, filled with the material 62, serves to provide the renewed interior structural support function for the cortical bone 28.

In this embodiment, the structure 56 can be made from an inert, durable, non-degradable plastic material, e.g., polyethylene and other polymers. Alternatively, the structure 56 can be made from an inert, bio-absorbable material, which degrades over time for absorption or removal by the body.

In this embodiment, the filling material 62 itself can serve as the expansion medium for the structure 56, to compact cancellous bone and form the cavity 60, to thereby perform both compaction and interior support functions. Alternatively, the structure 56 can be first expanded with another medium to compact cancellous bone and form the cavity 60, and the filling material 62 can be subsequently introduced after the expansion medium is removed from structure 56 to provide the interior support function. As another alternative, the filling material could comprise a two-part material including, but not limited to, settable polymers or calcium alginate. If desired, one part of the filling material could be utilized as the expansion medium, and the second part added after the desired cavity size is achieved.

The structure 56 can also be made from a permeable, semi-permeable, or porous material, which allows the transfer of medication contained in the filling material 62 into contact with cancellous bone through the wall of the structure 56. If desired, the material can comprise a membrane that allows osmotic and/or particulate transfer through the material, or the material can comprise a material that allows the medication to absorb into and/or diffuse through the material. Alternatively, medication can be transported through a porous wall material by creating a pressure differential across the wall of the structure 56.

As another alternative, fluids, cells and/or other materials from the patient's body can pass and/or be drawn through the material into the structure for various purposes including, but not limited to, fluid/cellular analysis, bony ingrowth, bone marrow harvesting, and/or gene therapy (including gene replacement therapy).

B. Bilateral Access

Figure 10:
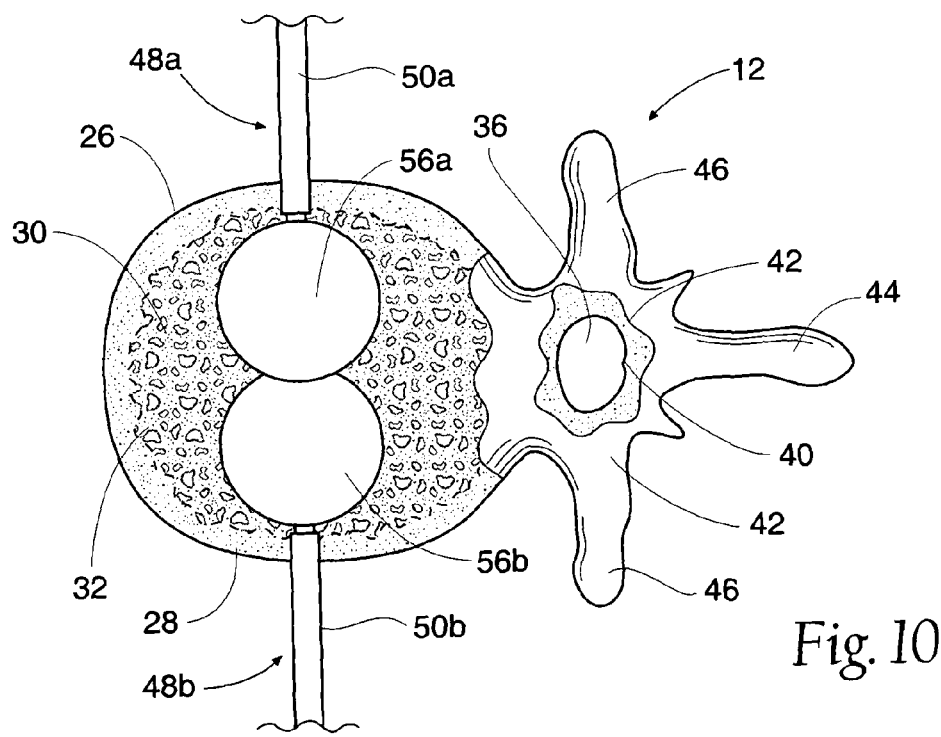
FIG. 10 is a coronal view of the vertebral body shown in FIG. 2, with two tools shown in FIGS. 4 and 5 deployed through bilateral accesses and in an expanded condition to compress cancellous bone and form adjoining, generally symmetric cavities.
Figure 11:
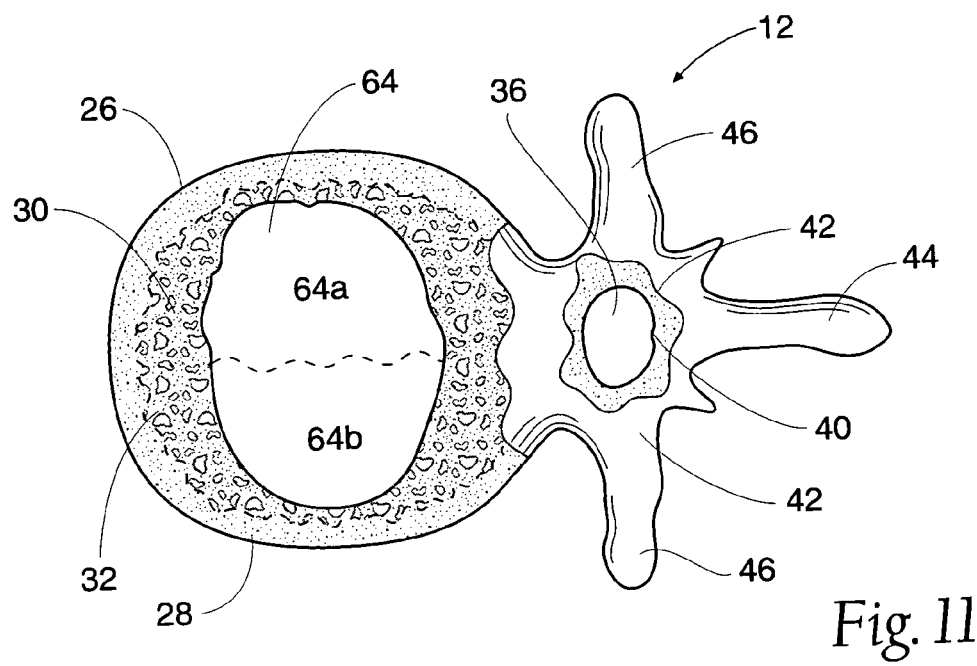
FIG. 11 is a coronal view of the vertebral body shown in FIG. 10, with the tools removed after formation of the generally symmetric cavities and the cavities filled with a material that strengthens the vertebral body.

As FIGS. 10 and 11 show, an enlarged cavity 64, occupying substantially all of the interior volume, can be created by the deployment of multiple expandable structures 56A and 56B through two lateral separate accesses PLA1 and PLA2, made in opposite lateral sides of a vertebral body 26. In FIG. 10, the expandable structures 56A and 56B are carried by separate tools 48A and 48B at the distal ends of catheter tubes 50A and 50B, which are separate and not joined together.

Expansion of the multiple expandable structures 56A and 56B forms two cavity portions 64A and 64B (shown in FIG. 11). The cavity portions 64A and 64B are transversely spaced within the cancellous bone 32. The transversely spaced cavity portions 64A and 64B preferably adjoin to form the single combined cavity 64 (shown in FIG. 11), into which a filling material is injected.

Alternatively (not shown), the transversely spaced cavity portions 64A and 64B can remain separated by a region of cancellous bone. The filling material is still injected into each cavity portion 64A and 64B.

FIG. 10 shows the structures 56A and 56B to possess generally the same volume and geometry, when substantially expanded. This arrangement provides a symmetric arrangement for compacting cancellous bone 32. A generally symmetric, enlarged cavity 64 (shown in FIG. 11) results.

Alternatively, the structures 56A and 56B may possess different volumes and/or geometries when substantially expanded, thereby presenting an asymmetric arrangement for compacting cancellous bone 32. A generally asymmetric cavity 66 (see, e.g., FIG. 12) results.

The selection of size and shape of the structures 56A and 56B, whether symmetric or asymmetric, depends upon the size and shape of the targeted cortical bone 28 and adjacent internal anatomic structures, or by the size and shape of the cavity 64 or 66 desired to be formed in the cancellous bone 32. It can be appreciated that the deployment of multiple expandable structures 56A and 56B makes it possible to form cavities 64 or 66 having diverse and complex geometries within bones of all types.

It has been discovered that compression fracture or collapse of one vertebral body can occur in combination with compression fracture or collapse of an adjacent vertebral body or bodies. For example, the failure of one vertebral body may alter loading of adjacent vertebral bodies, or can cause unequal loading of adjacent vertebral bodies, resulting in failure of one of more of the adjacent bodies as well. Because the factors which weaken and/or cause fracture of one vertebral body will often weaken and/or affect other vertebral bodies within the spinal column, these adjacent vertebral bodies are susceptible to fracture and/or collapse. In a similar manner, the treatment of a compression fracture of a single vertebral body may alter the loading of the adjacent vertebral bodies, possibly resulting in failure of one or more of the adjacent bodies. The treatment of two or more vertebral bodies during a single procedure may therefore be indicated.

Figure 13:
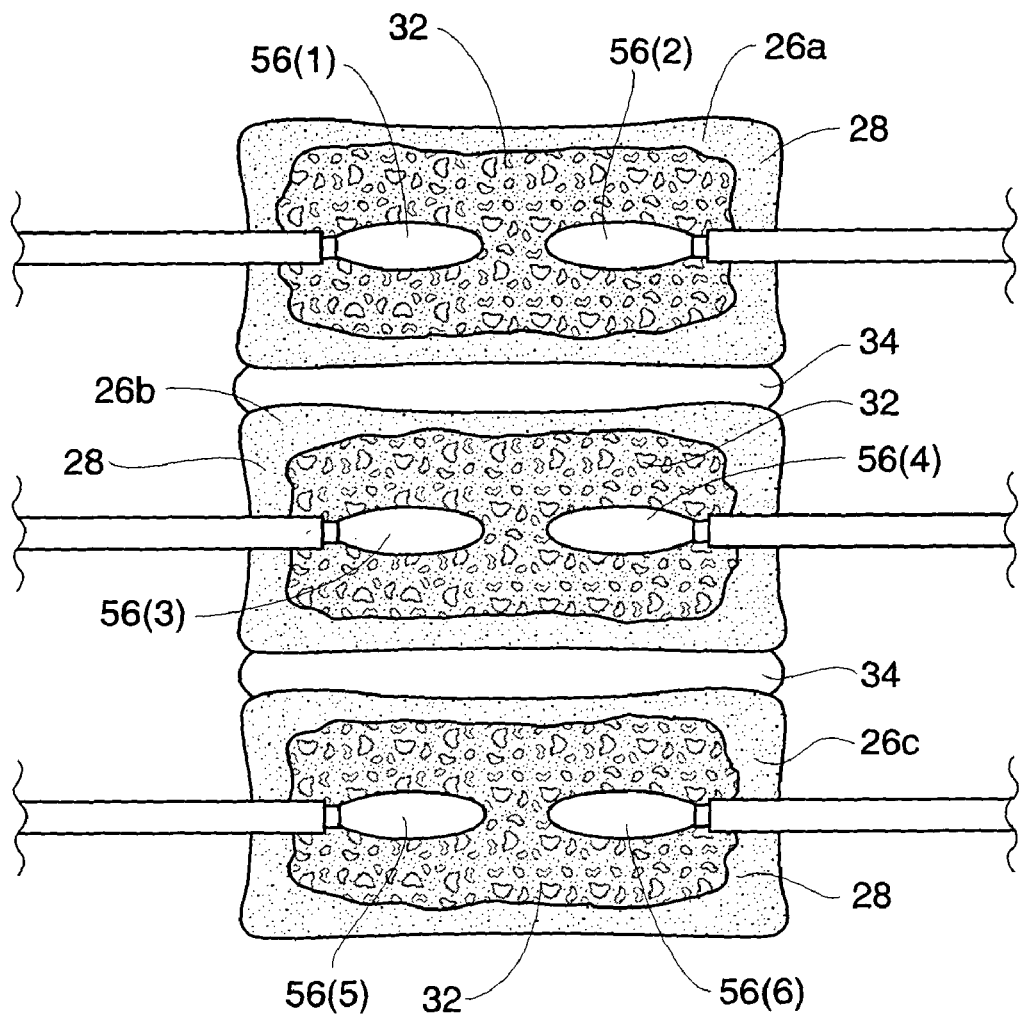
FIG. 13 is a anterior sectional view of three adjacent vertebral bodies, with six tools shown in FIGS. 4 and 5 deployed in collapsed conditions through two lateral accesses in each vertebral body.

FIG. 13 shows a procedure treating three adjacent vertebral bodies 26A, 26B, and 26C, each with bilateral accesses. As shown, the multiple bilateral procedure entails the deployment of six expandable structures 56(1) to 56(6), two in each vertebral body 26A, 26B, and 26C. As FIG. 13 shows, expandable structures 56(1) and 56(2) are bilaterally deployed in vertebral body 26A; expandable structures 56(3) and 56(4) are bilaterally deployed in vertebral body 26B; and expandable structures 56(5) and 56(6) are bilaterally deployed in vertebral body 26C.

The volume of a given cavity 64 formed in cancellous bone using multiple expandable structures (e.g., using a bilateral or other type of access) can be optimized by alternating the expansion of the multiple expandable structures deployed. For example, in the illustrated embodiment, in each vertebral body, one of the expandable structures 56(1) is first expanded, followed by the expansion of the other expandable body 56(2).

When pressure is first applied to expand a given structure 56(1) to 56(6), cancellous bone will begin to compact and/or cortical bone will begin to displace. A period of time follows in which the pressure within the structure 56(1) to 56(6) typically decays, as the cancellous bone relaxes, further compacts and/or cortical bone is further displaced. Pressure decay in one structure also typically occurs as the other expandable structure within the vertebral body is expanded. When pressure is again restored to the structure 56(1) to 56(6), further cancellous bone compaction and/or cortical bone displacement generally results. A further decay in pressure in the structure 56(1) to 56(6) will then typically follow. A decay of pressure will generally follow the application of pressure, until the cancellous bone is compacted a desired amount and/or cortical bone is displaced to a desired position.

Optimal cavity formation therefore occurs when each expandable structure 56(1) to 56(6) is allowed to expand in a sequential, step wise fashion. By allowing the pressure in each structure to decay before introducing additional pressure, the peak internal pressure experienced within each structure can be reduced, thereby reducing the potential for failure of the structure. FIGS. 14A to 14D more particularly demonstrate this step wise sequence of applying pressure to a given pair of expandable structures, e.g., 56(1) and 56(2), when deployed bilaterally in a vertebral body 26A. It should be appreciated, that the step wise application of pressure can also be used when a single expandable body is deployed, or when one or more expandable structures are deployed in other than in a lateral fashion, e.g., using a transpedicular, extrapedicular, or anterior access.

It should also be understood that expandable structures incorporating non-compliant materials could be used in similar manners to accomplish various objectives of the present invention. For example, where the expandable structures comprise non-compliant materials, such structures could be expanded within the cancellous bone in the previously described manner to compress cancellous bone, create a cavity and/or displace cortical bone. Depending upon the density and strength of the cancellous and/or cortical bone, the described application of additional pressure to the structures could cause a similar cycle of volumetric growth and pressure decay. Upon reaching maximum capacity and/or shape of the structures, the introduction of additional pressure would typically result in little volumetric expansion of the structures.

Figure 14A:
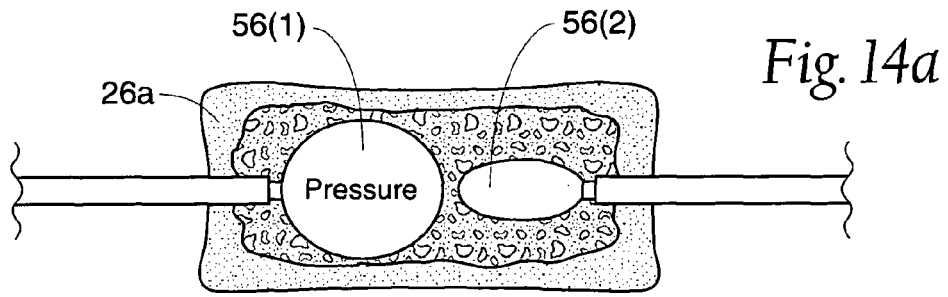
FIGS. 14A to 14D are schematic anterior views of one of the vertebral bodies shown in FIG. 13, showing the alternating, step wise application of pressure to the expandable structures to compress cancellous bone and form adjacent cavities.

In FIG. 14A, the expandable structures 56(1) and 56(2) have been individually deployed in separate lateral accesses in vertebral body 26A. The expandable structures 56(3)/56(4) and 56(5)/56(6) are likewise individually deployed in separate lateral accesses in vertebral bodies 26B and 26C, respectively, as FIG. 13 shows. Representative instruments for achieving these lateral accesses will be described later.

Once the expandable structures 56(1) to 56(6) are deployed, the physician successively applies pressure successively to one expandable structure, e.g., 56(1), 56(3), and 56(5), in each vertebral body 26A, 26B, and 26C. FIG. 14A shows the initial application of pressure to structure 56(1). Alternatively, the physician can deploy expandable structures in a single vertebral body, expand those structures as described herein, and then deploy and expand expandable structures within another vertebral body. As another alternative, the physician can deploy the expandable structures in a single vertebral body, expand those structures as described herein, fill the cavities within that vertebral body, and then deploy and expand expandable structures within another vertebral body.

Figure 14B:
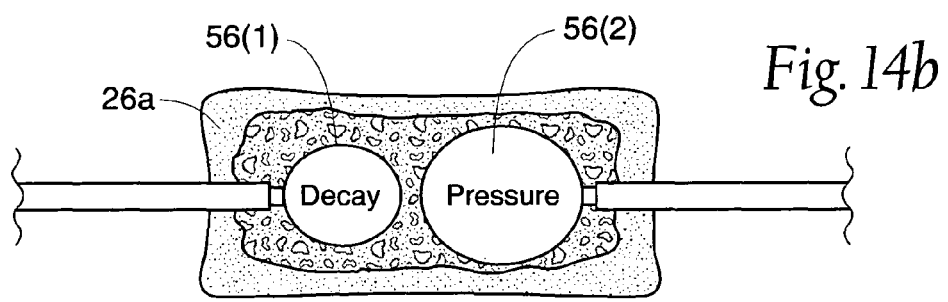

The pressure in the structures 56(1), 56(3), and 56(5) will, over time decay, as the cancellous bone in each vertebral body 26A, 26B, and 26C relaxes, further compresses and/or cortical bone displaces in the presence of the expanded structure 56(1), 56(3), and 56(5), respectively. As pressure decays in the structures 56(1), 56(3), and 56(5), the physician proceeds to successively apply pressure to the other expandable structures 56(2), 56(4), and 56(6) in the same vertebral bodies 26A, 26B, and 26C, respectively. FIG. 14B shows the application of pressure to structure 56(2), as the pressure in structure 56(1) decays.

Figure 14C:
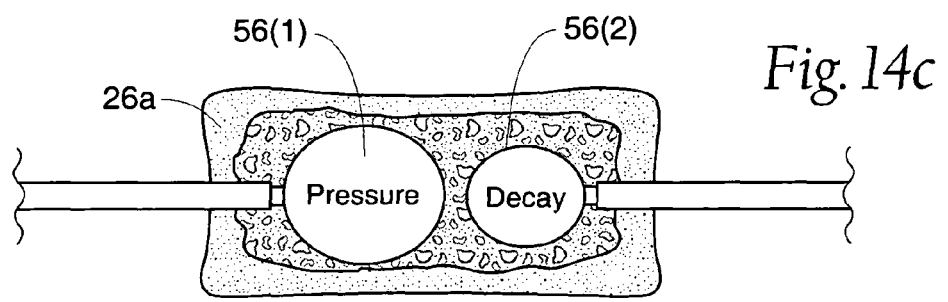
Figure 14D:
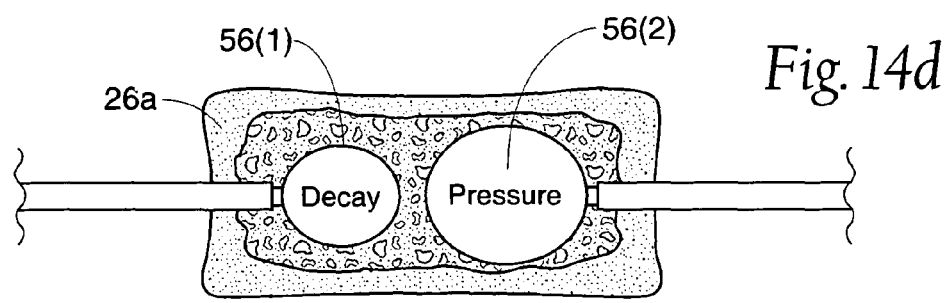

The pressure in each structure 56(2), 56(4), and 56(6) will likewise decay over time, as the cancellous bone in each vertebral body 26A, 26B, and 26C is compressed in the presence of the expanded structure 56(2), 56(4), and 56(6), respectively. As pressure decays in the structures 56(2), 56(4), and 56(6), the physician proceeds to successively apply additional pressure to the other expandable structures 56(1), 56(3), and 56(5) in the vertebral bodies 26A, 26B, and 26C, respectively. The introduction of additional pressure in these structures 26(1), 26(3), and 26(5) further enlarges the volume of the cavity portions formed as a result of the first application of pressure. FIG. 14C shows the introduction of additional pressure to structure 56(1) as pressure decays in structure 56(2).

Pressure, once applied, will typically continue to decay in each structure 56(1)/56(2), 56(3)/56(4), and 56(5)/56(6), as the cancellous bone relaxes, continues to compact and/or cortical bone is displaced. As pressure is successively applied and allowed to decay, the volumes of the cavity portions also successively enlarge, until desired cavity volumes have been achieved in the vertebral bodies 26A, 26B, and 26C and/or desired displacement of cortical bone has been achieved.

This deliberate, alternating, step wise application of pressure, in succession first to the structures 26(1)/26(3)/26(5) and then in succession to the structures 26(2)/26(4)/26(6) in the three vertebral bodies 26A/B/C continues until a desired endpoint for each of the vertebral bodies 26A, 26B, and 26C is reached. In one embodiment, the desired cavity volume is achieved when cancellous bone is uniformly, tightly compacted against surrounding cortical bone. In an alternative embodiment, desired cavity volume is achieved when a significant pressure decay no longer occurs after the introduction of additional pressure, such as where substantially all of the cancellous bone has been compressed and/or the cortical bone does not displace further.

It should be understood that compaction of cancellous bone may be non uniform due to varying factors, including local variations in bone density. In addition, it should be understood that desired displacement of cortical bone can be accomplished in a similar manner, either alone or in combination with compaction of cancellous bone. By utilizing multiple structures to displace the cortical bone, a maximum amount of force can be applied to the cortical bone over a larger surface area, thereby maximizing the potential for displacement of the cortical bone while minimizing damage to the cortical bone from contact with the structure(s) and/or cancellous bone.

Once the desired volume for each cavity 64 and/or desired displacement of cortical bone in each vertebral body 26A, 26B, and 26C is reached, the physician begins the task of conveying a selected filling material 62 into each formed cavity 64. It should be appreciated that the cavities 64 can be filled with filling material 62 essentially in any order, and it is not necessary that all expandable structures be expanded to form all the cavities 64 before the filling material is conveyed into a given cavity.

In one embodiment, the filling material is conveyed in alternating steps into the cavity portions 64A and 64B of each vertebral body 26A, 26B, and 26C. In this technique, the cavity volumes 64A formed by the expandable structures 56(1), 56(3), and 56(5) are filled in succession before the cavity volumes 64B formed by the expandable structures 56(2), 56(4), and 56(6) are filled in succession.

Figure 15A:
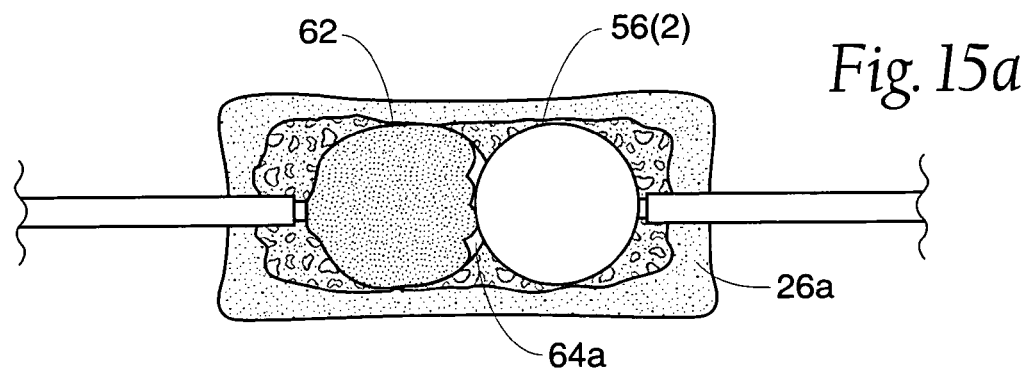
FIGS. 15A and 15B are schematic anterior views of one of the vertebral bodies shown in FIGS. 14A to 14D, depicting the alternating sequence of filling the adjacent cavities with a material to strength the vertebral body.
Figure 15B:
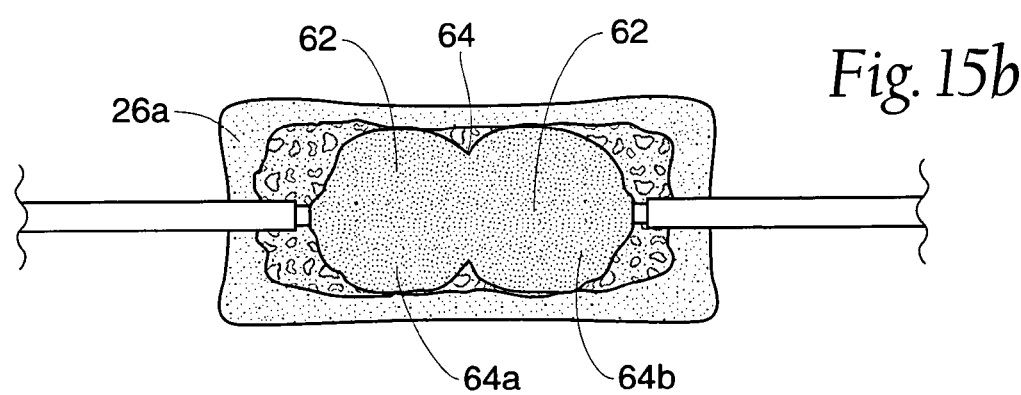

FIGS. 15A and 15B show this embodiment of a filling sequence for the vertebral body 26A. The vertebral bodies 26B and 26C are filled in like manner. In the vertebral body 26A, the expandable structure 56(1) is deflated and removed. The filling material 62 is then conveyed into the corresponding cavity portion 64A. Next, in the vertebral body 26B, the expandable structure 56(3) is deflated and removed, and the filling material 62 conveyed into the corresponding cavity portion 64A. Next, in the vertebral body 26C, the expandable structure 56(5) is deflated and removed, and the filling material 62 conveyed into the corresponding cavity portion 64A. The expandable structures 56(2), 56(4), and 56(6) are left inflated within the respective vertebral bodies 26A, 26B, and 26C during this portion of the filling process.

The physician waits for the filling material 62 conveyed into the vertebral bodies 26A, 26B, and 26C to harden. Then, as FIG. 15B shows for the vertebral body 26A, the expandable structure 56(2) is deflated and removed. The filling material 62 conveyed into the corresponding cavity portion 64B. Next, in the vertebral body 26B, the expandable structure 56(4) is deflated and removed, and the filling material 62 conveyed into the corresponding cavity portion 64B. Last, in the vertebral body 26C, the expandable structure 56(6) is deflated and removed, and the filling material 62 conveyed into the corresponding cavity portion 64B. The above sequence allows a single batch of the filling material 62 to be mixed and expeditiously dispensed to fill multiple cavities 64.

In one alternative embodiment, the filling material is conveyed in alternating steps into the cavity portions of each respective vertebral body prior to filling the next vertebral body. In this technique, the expandable structure 56(1) is removed from the vertebral body, and filling material is conveyed into the corresponding cavity portion 64A. The expandable structure 56(2) is then removed from the vertebral body, and filling material is conveyed into the corresponding cavity portion 64B. If desired, the filling material can be allowed to harden to some degree before the expandable structure 56(2) is removed from the vertebral body. The process is then repeated for each remaining vertebral body to be treated. In this embodiment, the vertebral body is desirably substantially supported by the filling material and/or an expandable structure during the filling process, which reduces and/or eliminates the opportunity for the cavity to collapse and/or cortical bone to displace in an undesired direction during the filling operation.

III. Instruments for Establishing Bilateral Access

During a typical bilateral procedure, a patient lies on an operating table. The patient can lie face down on the table, or on either side, or at an oblique angle, depending upon the physician's preference.

A. Establishing Multiple Accesses

1. Use of Hand Held Instruments

Figure 16A:
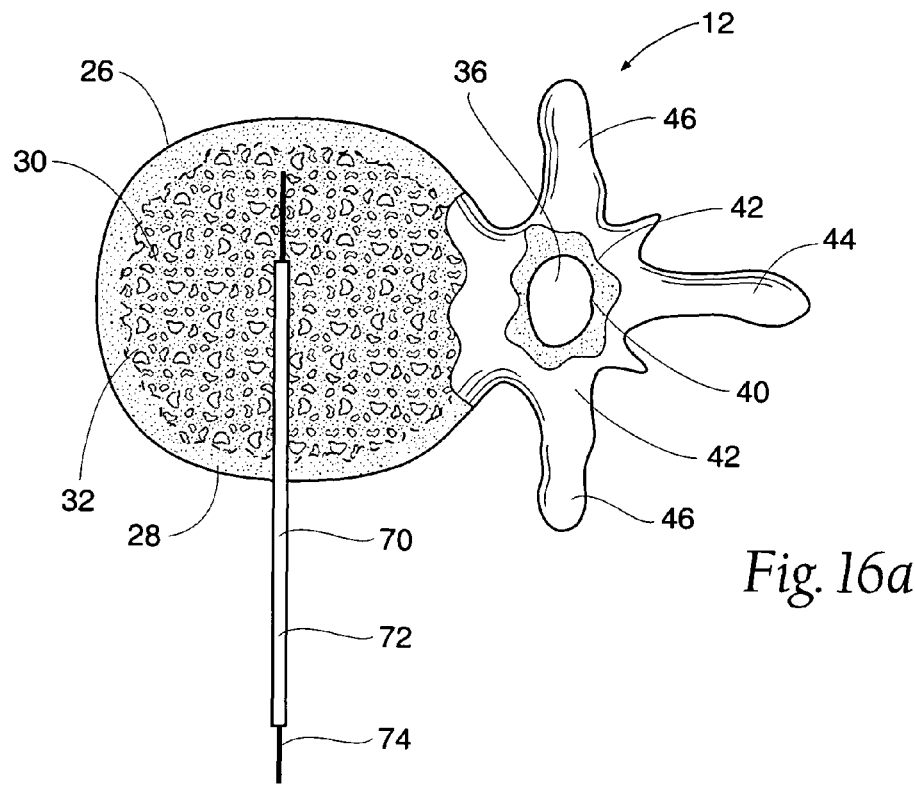
FIGS. 16A to 16I are coronal views of a vertebral body as shown in FIGS. 14A to 14D and 15A and 15B, showing tools deployed to create a lateral access to compress cancellous bone in a vertebral body to form an interior cavity, which is filled with a material to strengthen the vertebral body.

For each access (see FIG. 16A), the physician introduces a spinal needle assembly 70 into soft tissue ST in the patient's back. Under radiologic or CT monitoring, the physician advances the spinal needle assembly 70 through soft tissue down to and into the targeted vertebral body 26. The physician can also employ stereotactic instrumentation to guide advancement of the spinal needle assembly 70 and subsequent tools during the procedure. In this arrangement, the reference probe for stereotactic guidance can be inserted through soft tissue and implanted on the surface of the targeted vertebral body. The entire procedure can also be monitored using tools and tags made of non-ferrous materials, e.g., plastic or fiber composites, such as those disclosed in U.S. Pat. Nos. 5,782,764 and 5,744,958, which are each incorporated herein by reference, which would be suitable for use in a computer enhanced, whole-room. MRI environment.

The physician will typically administer a local anesthetic, for example, lidocaine, through the assembly 70. In some cases, the physician may prefer other forms of anesthesia.

The physician directs the spinal needle assembly 70 to penetrate the cortical bone 28 and the cancellous bone 32 through the side of the vertebral body 26. Preferably the depth of penetration is about 60% to 95% of the vertebral body 26.

The physician holds the stylus 72 and withdraws the stylet 74 of the spinal needle assembly 70. As FIG. 1.6B shows, the physician then slides a guide pin instrument 76 through the stylus 72 and into the cancellous bone 32. The physician now removes the stylus 72, leaving the guide pin instrument 76 deployed within the cancellous bone 32.

Figure 16B:
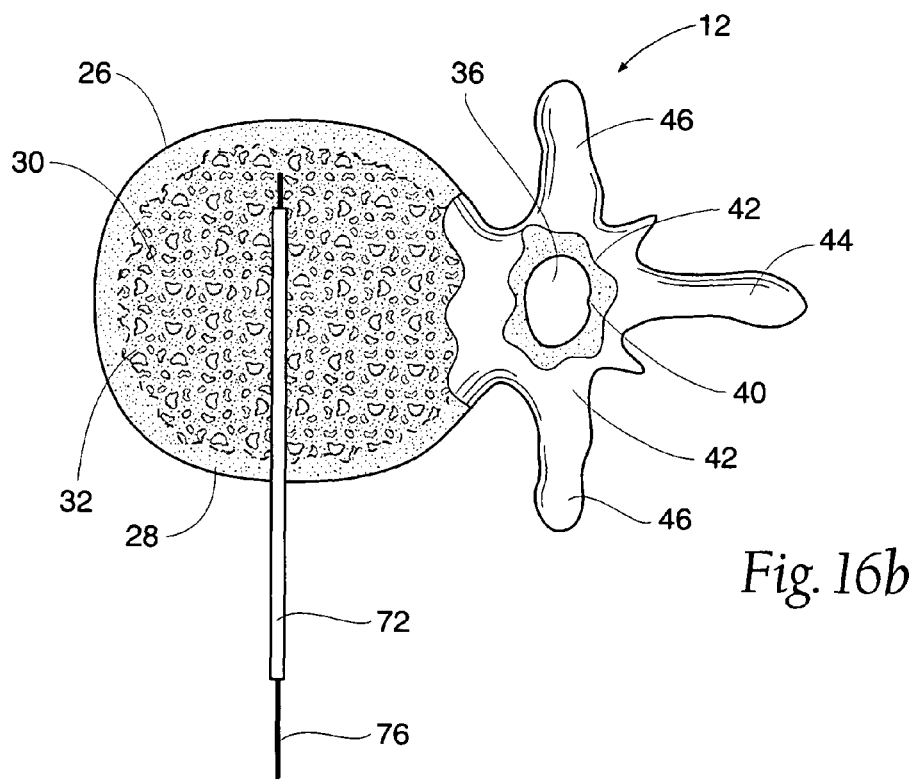
Figure 16C:
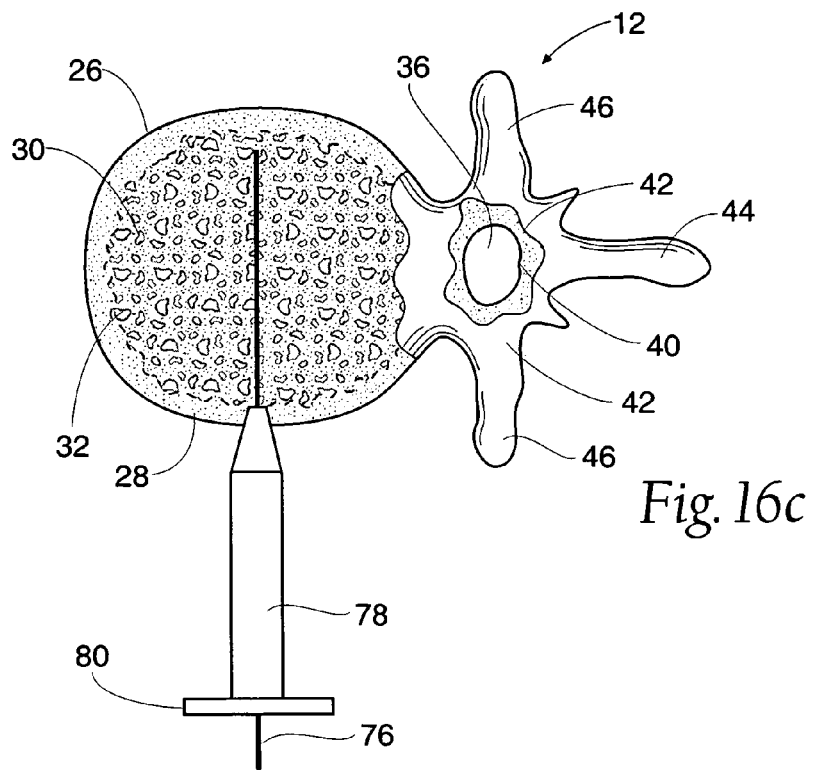

The physician next slides an obturator instrument 78 over the guide pin instrument 76, distal end first, as FIG. 16C shows. The physician can couple the obturator instrument 78 to a handle 80, which facilitates manipulation of the instrument 78.

The physician makes a small incision in the patient's back. The physician twists the handle 80 while applying longitudinal force to the handle 80. In response, the obturator instrument 78 rotates and penetrates soft tissue through the incision. The physician may also gently tap the handle 80, or otherwise apply appropriate additional longitudinal force to the handle 80, to advance the obturator instrument 78 through the soft tissue along the guide pin instrument 76 down to the cortical bone entry site. The physician can also tap the handle 80 with an appropriate striking tool to advance the obturator instrument 78 into a side of the vertebral body 26 to secure its position.

Figure 17:
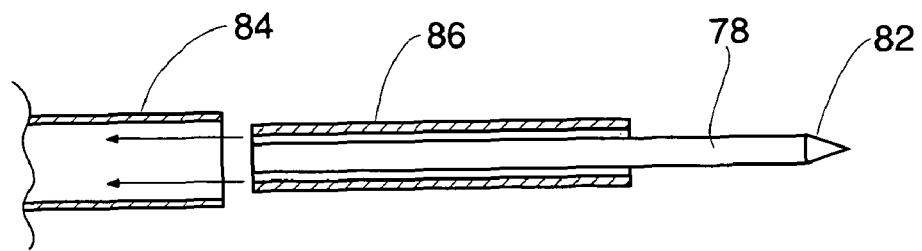
FIG. 17 is an exploded side section view of a reduced diameter obturator instrument with associated centering sleeve, which can be deployed to create access in a vertebral body, particularly through a pedicle.

The obturator instrument 78 shown in FIG. 16C has an outside diameter that is generally well suited for establishing a lateral access. However, if access is desired through the more narrow region of the vertebral body 26, e.g., a pedicle 42 (called transpedicular access), the outside diameter of the obturator instrument 78 can be reduced (as FIG. 17 shows). The reduced diameter of the obturator instrument 78 in FIG. 17 mediates against damage or breakage of the pedicle 42. The reduced diameter obturator instrument 78 shown in FIG. 17 includes a pointed tip 82 to help secure its position against cortical bone 28. It should be understood that the disclosed methods and devices are well suited for use in conjunction with other approach paths, such as pedicular, extra-pedicular, posterolateral and anterior approaches, with varying results.

The physician then proceeds to slide the handle 80 off the obturator instrument 78 and to slide a cannula instrument 84 over the guide pin instrument 76 and, further, over the obturator instrument 78. If desired, the physician can also couple the handle 80 to the cannula instrument 84, to apply appropriate twisting and longitudinal forces to rotate and advance the cannula instrument 84 through soft tissue ST over the obturator instrument 78. When the cannula instrument 84 contacts cortical bone 28, the physician can appropriately tap the handle 80 with a striking tool to advance the end surface into the side of the vertebral body 26 to secure its position.

When a reduced diameter obturator 78 is used, as shown in FIG. 17, the cannula instrument 84 can carry a removable inner sleeve 86 (as FIG. 17 also shows) to center the cannula instrument 84 about the reduced diameter obturator instrument 78 during passage of the cannula instrument 84 to the treatment site.

The physician now withdraws the obturator instrument 78, sliding it off the guide pin instrument 76, leaving the guide pin instrument 76 and the cannula instrument 84 in place. When a reduced diameter obturator instrument 78 is used, the physician can remove the inner centering sleeve 86.

Figure 16D:
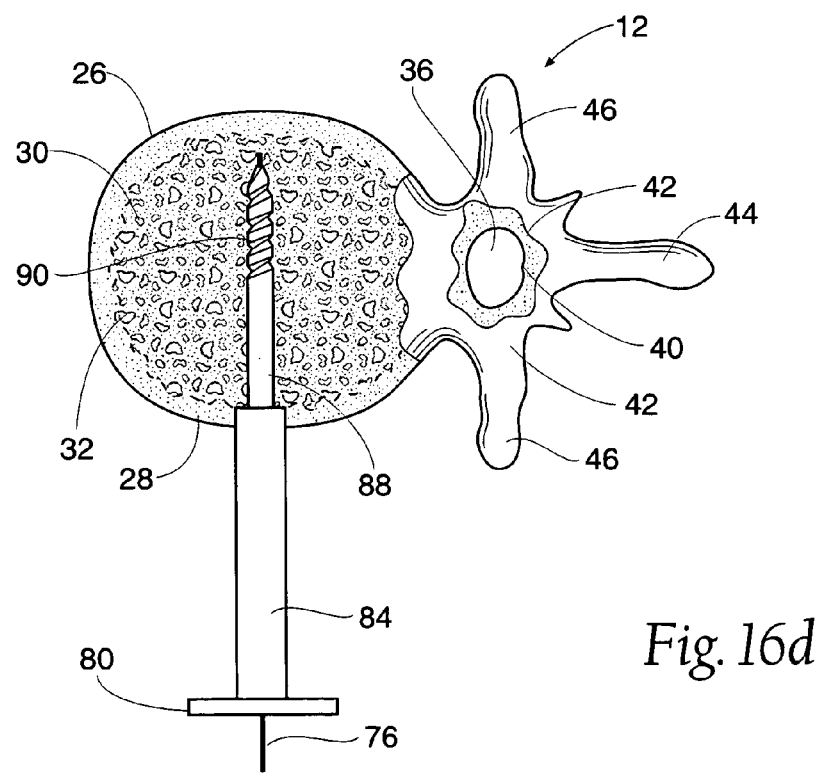

As FIG. 16D shows, the physician slides a drill bit instrument 88 over the guide pin instrument 76, distal end first, through the cannula instrument 84, until contact between the machined or cutting edge 90 of the drill bit instrument 88 and cortical bone 28 occurs. The physician then couples the drill bit instrument 88 to the handle 80.

Guided by X-ray (or another external visualizing system), the physician applies appropriate twisting and longitudinal forces to the handle 80, to rotate and advance the machined edge 90 of the drill bit instrument 88 to open a lateral passage PLA through the cortical bone 28 and into the cancellous bone 32. The drilled passage PLA preferably extends no more than 95% across the vertebral body 26.

Figure 18A:
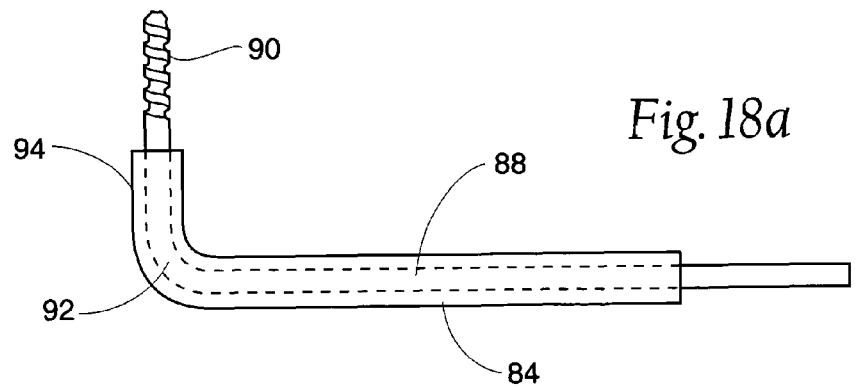
FIG. 18A is a side section view of a drill bit instrument that can be deployed to create access to a vertebral body, the drill bit instrument having a flexible shaft and deployed through a cannula instrument having a deflected end.

As FIG. 18A shows, the drill bit instrument 88 can include a flexible shaft portion 92 to aid in its manipulation. The flexible shaft portion 92 allows the cutting edge 90 of the instrument 88 to flex relative to the axis of the instrument. As FIG. 18A also shows, the cannula instrument 84 can, if desired, include a deflector element 94 on its distal extremity, to flex the flexible shaft portion 92 and guide the cutting edge 90 along a desired drill axis. Desirably, in such a flexible embodiment the drill bit instrument 88 is made of a flexible plastic material, e.g., polyurethane, or a flexible metal material encapsulated in or surrounding a plastic material, to possess sufficient torsional rigidity to transmit rotating cutting force to bone.

Figure 18B:
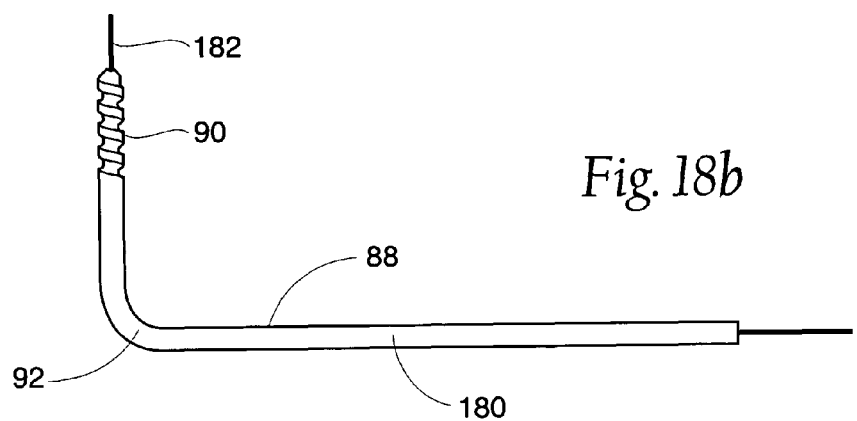
FIG. 18B is a side view of a drill bit instrument that can be deployed to create access to a vertebral body, the drill bit instrument having a flexible shaft and deployed over a guide wire having a deflected end.

Alternatively, as FIG. 18B shows, the drill bit instrument 88 can include an interior lumen 180 to accommodate passage of a guide wire 182. In this arrangement, the flexible shaft portion 92 conforms to the path presented by the guide wire 182. The guide wire 182, for example, can be pre-bent, to alter the path of the cutting edge 90 after it enters the vertebral body. Alternatively, the guide wire can be made of memory wire, shape memory alloys (including nickel-titanium, copper or iron based alloys, to name a few), or comprise a self-steering guiding catheter.

Figure 18C:
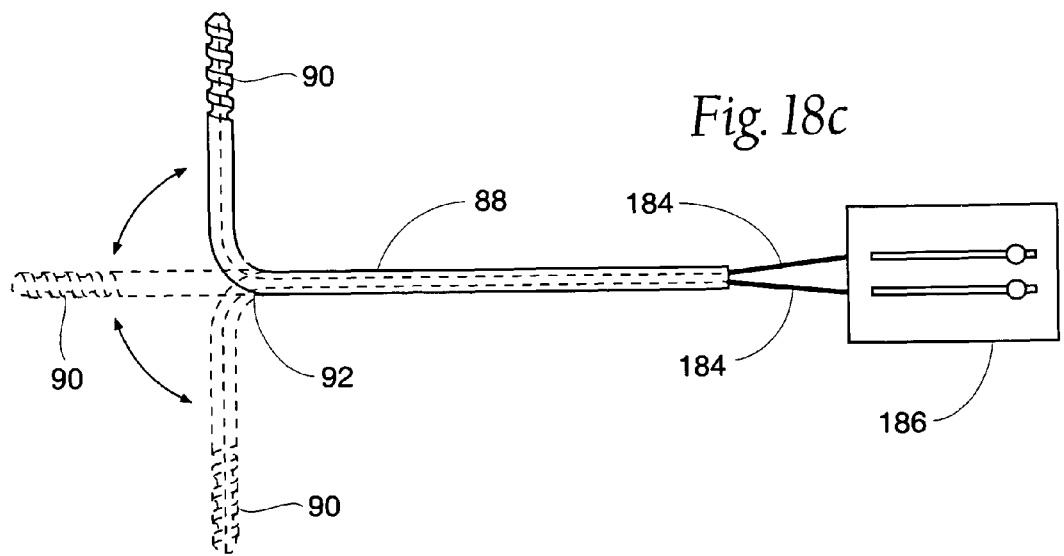
FIG. 18C is a side view of a drill bit instrument that can be deployed to create access to a vertebral body, the drill bit instrument having a flexible shaft and including steering wires to deflect its distal end.

Still alternatively, as FIG. 18C shows, the drill bit instrument 88 itself can carry interior steering wires 184. The steering wires 184 are operated by the physician using an external actuator 186, to deflect the flexible shaft portion 92, and with it the cutting edge, without aid of a guide wire and/or cannula instrument 84.

Further details regarding the formation of cavities within cancellous bone, which are not symmetric, with relation to the axis of a vertebral body, can be found in U.S. Pat. No. 5,972,015, entitled "Expandable Asymmetric Structures for Deployment in Interior Body Regions," which is incorporated herein by reference.

Figure 16E:
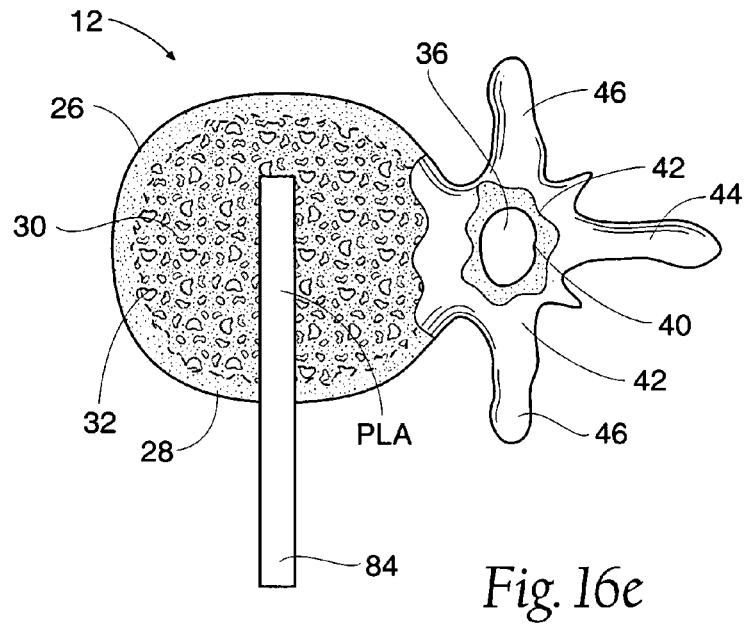

Once the passage PLA in cancellous bone 32 has been formed, the physician removes the drill bit instrument 88 and the guide pin instrument 76, leaving only the cannula instrument 84 in place, as FIG. 16E shows. The passage PLA made by the drill bit instrument 88 remains. Subcutaneous lateral access to the cancellous bone 32 has been accomplished.

The physician repeats the above described sequence of steps, as necessary, to form each access desired. In FIG. 13, six accesses are made.

2. Using Composite Hand Held Instruments

Other forms of hand held instruments may be used to provide access.

Figure 27:
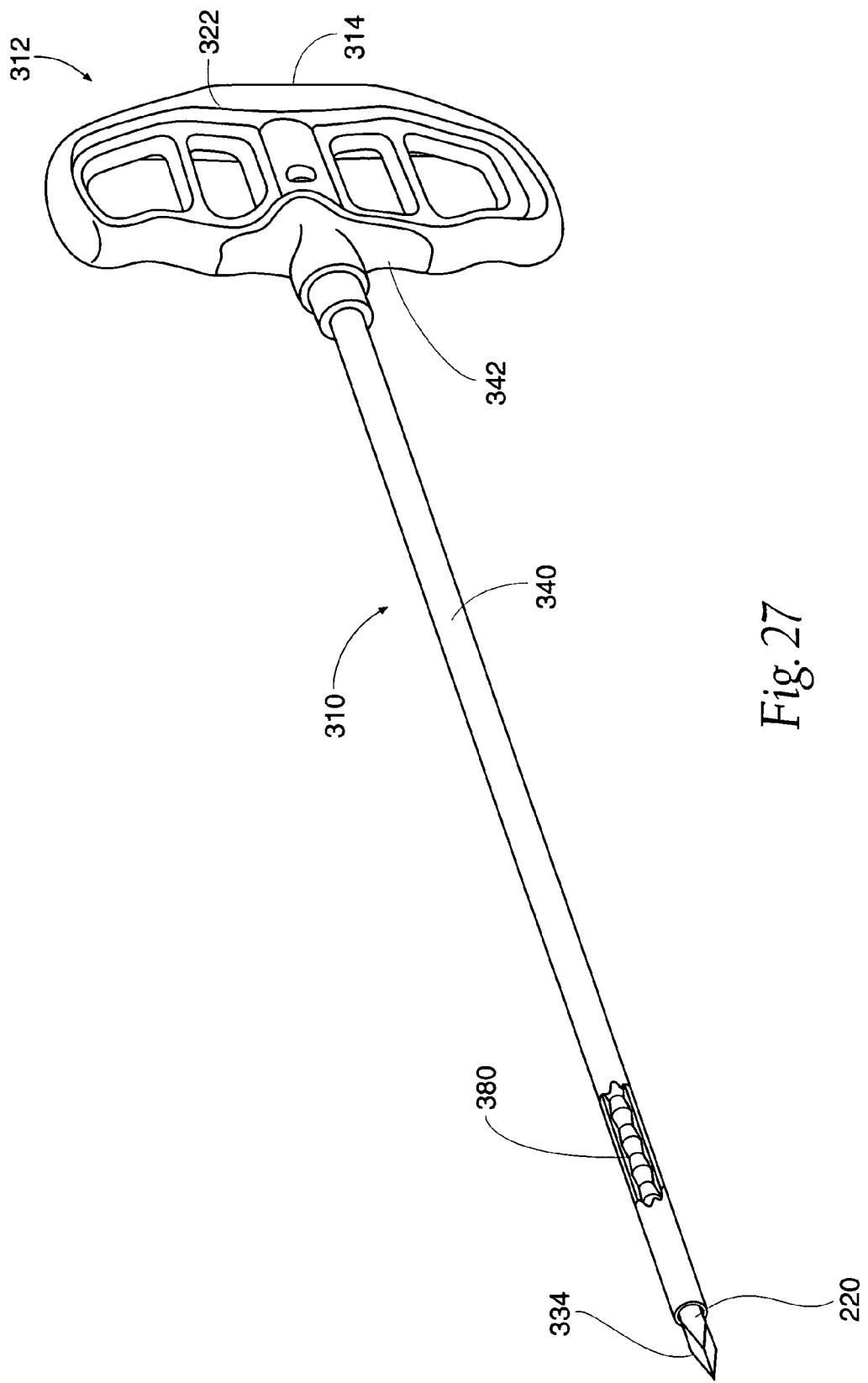
FIG. 27 is a perspective view of a composite tool that includes a trocar and a cannula instrument.
Figure 28:
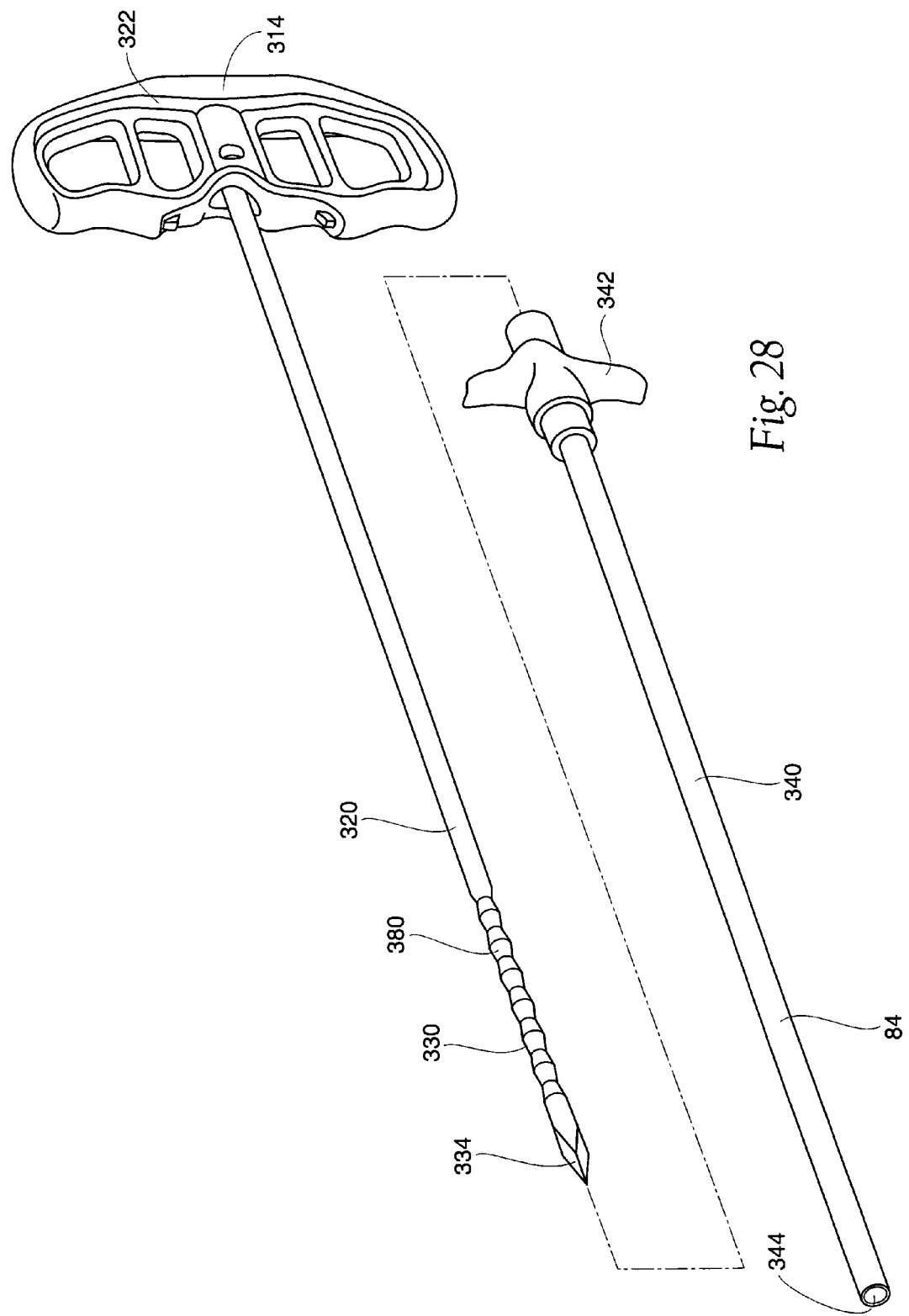
FIG. 28 is a perspective view of the composite instrument shown in FIG. 27, with the trocar separated from the cannula instrument.
Figure 29A:
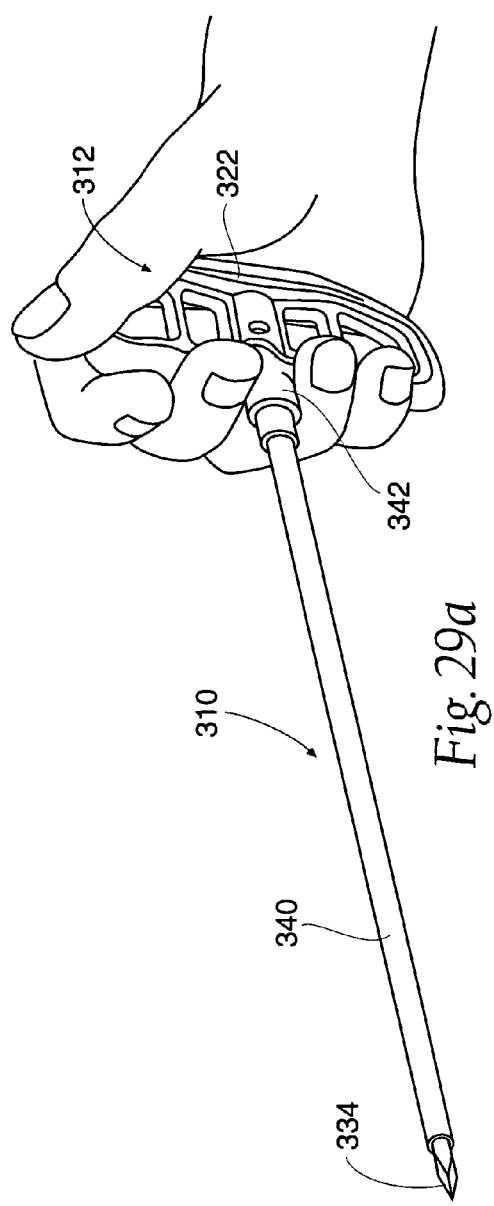
FIG. 29A is a perspective view of a hand engaging the composite handle of the tool shown in FIG. 27.
Figure 29B:
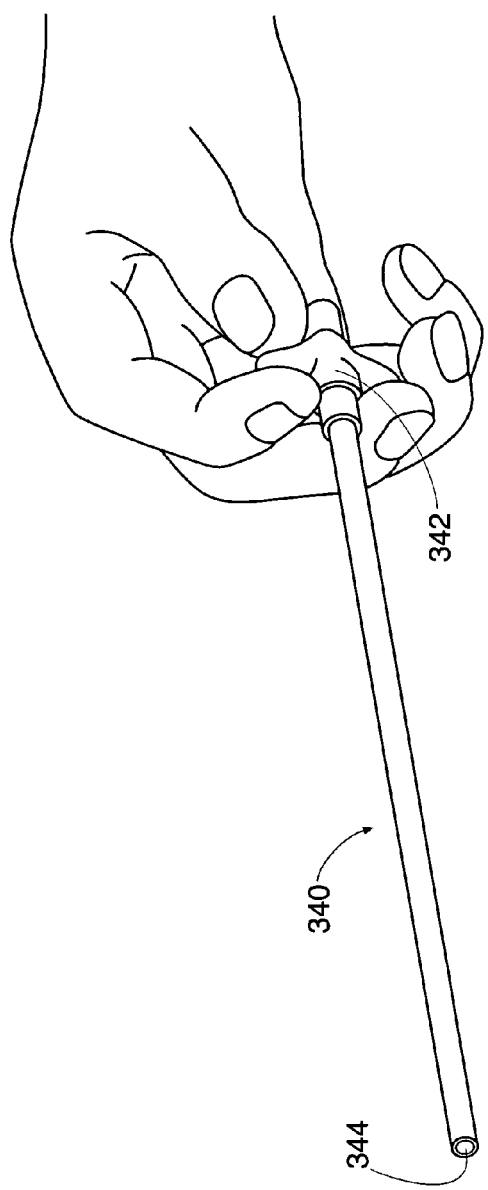
FIG. 29B is a perspective view of a hand engaging the handle of the cannula instrument when separated from the trocar.

For example, FIGS. 27 and 28 show a composite instrument 310 that can be used for this purpose. The composite instrument 310 includes a trocar instrument 320 and a cannula instrument 340. The composite instrument 310 also includes a composite handle 312 comprising a first handle 322 and a second handle 342. The composite handle 312 aids a physician in manipulating the composite instrument 310. Still, as FIGS. 29A and 29B show, a physician can also desirably use the first handle 322 to independently manipulate the trocar instrument 320 or the second handle 342 to independently manipulate the cannula instrument 340 during use.

The trocar instrument 320 comprises a trocar 330 having a distal end that is tapered to present a penetrating surface 334. In use, the penetrating surface 334 is intended to penetrate soft tissue and/or bone in response to pushing and/or twisting forces applied by the physician at the first handle 322, or the composite handle 312.

The cannula instrument 340 performs the function of the cannula instrument 84 previously described, but also includes the handle 342, which mates with the handle 322 to form the composite handle 312. In this embodiment, the cannula instrument 84 is desirably somewhat larger in diameter than and not as long as the trocar 330. The cannula instrument 84 includes an interior lumen 344 that is sized to accept the trocar 330. The size of the interior lumen 344 desirably allows the cannula instrument 84 to slide and/or rotate relative to the trocar 330, and vice versa. The distal end 354 of the cannula instrument 84 presents an end surface 360 that desirably presents a low-profile surface, which can penetrate soft tissue surrounding the trocar 330 in response to pushing and/or twisting forces applied at the composite handle 312 or the second handle 342.

Figure 30:
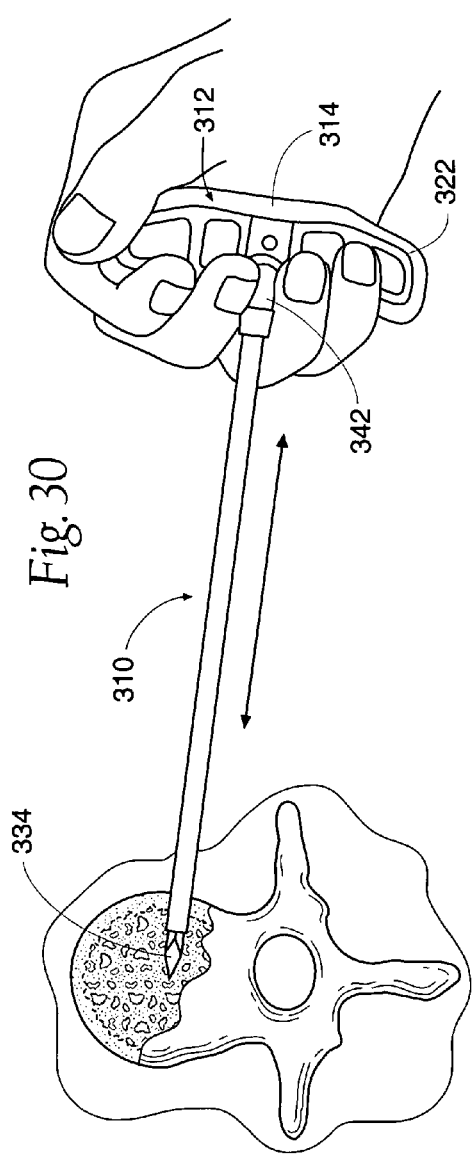
FIG. 30 is a top view showing deployment of the composite instrument shown in FIG. 27 in a vertebral body, by using the composite handle to apply an axial and/or torsional force.

In use, as shown in FIG. 30, the physician directs the composite instrument 310 such that the trocar 330 and the cannula instrument 84 penetrate the cortical bone and the cancellous bone of the targeted vertebra. If desired, the physician can twist the composite handle 312 while applying longitudinal force to the handle 312. In response, the penetrating end surface 334 of the trocar 330, and the end surface of the cannula instrument 84 rotate and penetrate soft tissue and/or bone.

If penetration through the cortical bone and into the cancellous bone is not achievable by manual advancement of the composite instrument 310, a physician can continue penetration by gently striking a striking plate 314 on the composite handle 312 with a blunt instrument such as a surgical hammer (not shown), or otherwise applying appropriate additional longitudinal force to the composite handle 312, to advance the distal end 334 of the trocar 330 and the end surface of the cannula instrument 84.

If desired, the physician can utilize a spinal needle assembly 70, as already described, to initially access the vertebral body. In this arrangement, the composite instrument 310 is later guided through soft tissue and into the targeted vertebra body along the stylet 74, which (in this arrangement) passes through an interior lumen in the trocar 330 (not shown). Once the trocar 330 has sufficiently penetrated cortical bone, the physician can withdraw the stylet 74, thereby arriving at the step in the procedure shown in FIG. 30.

After penetrating the cortical bone, the physician may continue advancing the composite instrument 310 through the cancellous bone of the vertebral body to form the passage through the cancellous bone, as already described. The trocar 330 may then be withdrawn from the cannula instrument 84. The cannula instrument 84 remains to provide access to the passage formed in the interior of the vertebral body, in the manner previously described.

Figure 31:
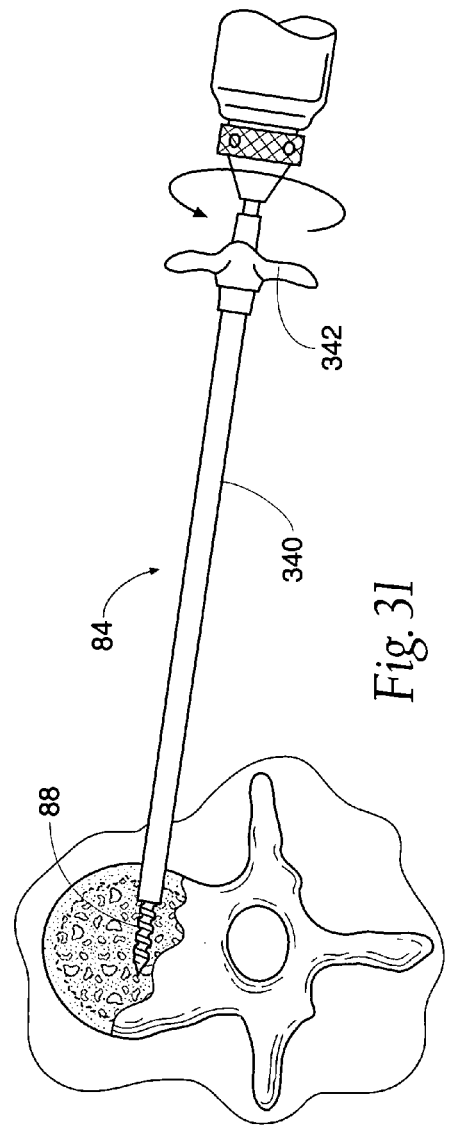
FIG. 31 is a top view of the vertebral body, showing deployment of a drill bit through a cannula instrument, which forms a part of the composite tool shown in FIG. 27.

Alternatively, after penetrating the cortical bone, the physician may choose to withdraw the trocar 330 from the cannula 50 and form the passage in the cancellous bone using a drill bit instrument 88, as FIG. 31 shows. In such a case, the physician removes the trocar 330 and, in its place, advances the drill bit instrument 88 through the cannula instrument 84, as FIG. 31 shows.

With the removal of the drill bit instrument 88, access to the cancellous bone has been accomplished.

Further details about the structure and use of the composite instrument 310 are found in copending U.S. patent application Ser. No. 09/421,635, filed Oct. 19, 1999, and entitled "Hand-Held Instruments that Access Interior Body Regions," which is incorporated herein by reference.

3. Breach Prevention and Plugging

Figure 19:
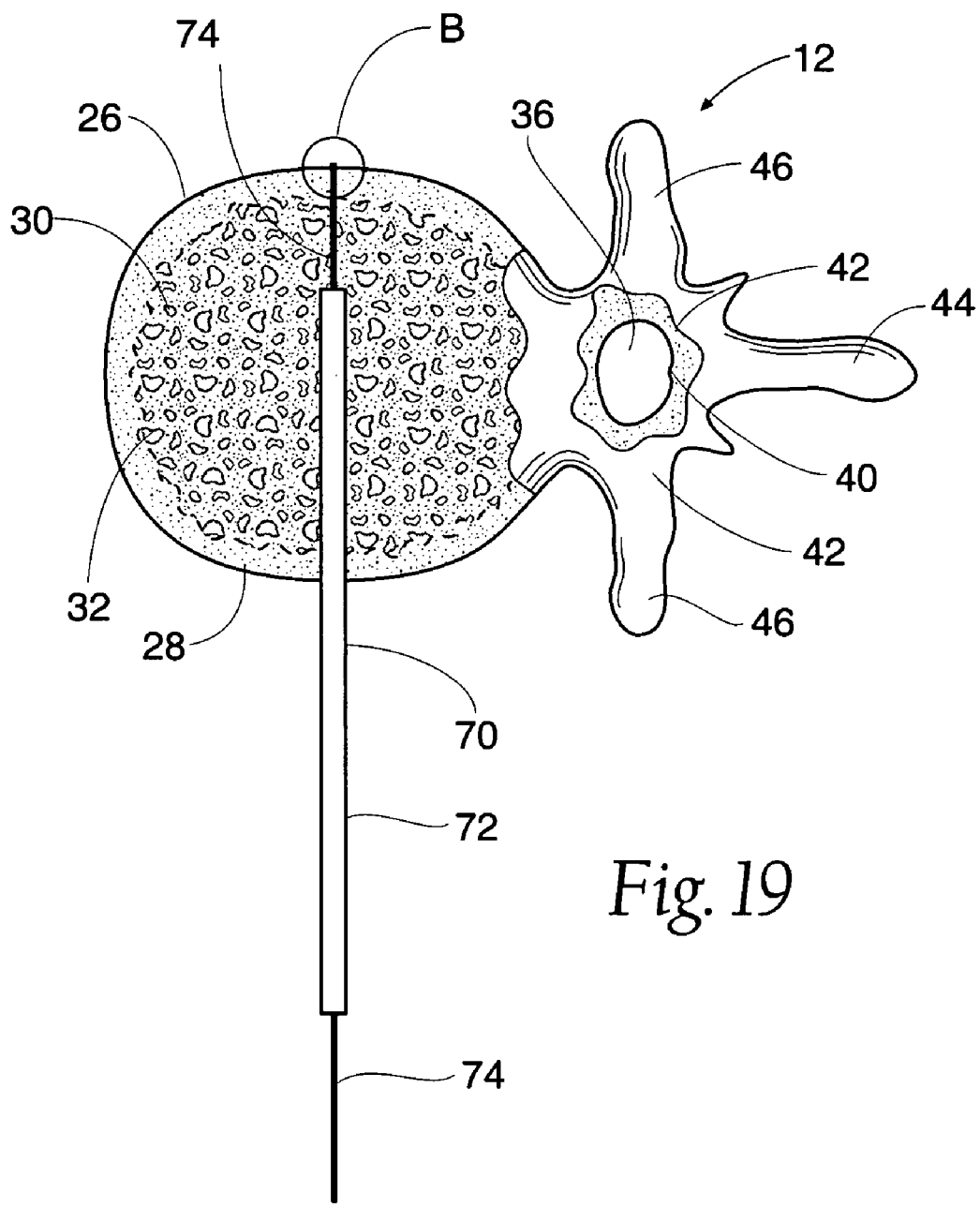
FIG. 19 is a coronal view of a vertebral body showing the deployment of a spinal needle tool in a, manner that creates a breach in an anterior cortical wall of the vertebral body.

To create access into the vertebral body in the manners shown in FIGS. 16A to 16D, the physician typically advances a stylet 74 of the spinal needle assembly 70 and also the cutting edge of the drill bit instrument 88 a significant distance into the cancellous bone 32, as FIGS. 16B and 16D show, toward cortical bone 28 on the anterior wall of the vertebral body 26. The density of the cancellous bone 32 desirably offers resistance to the passage of these instruments, to thereby provide tactile feed back to the physician, which aids in guiding their deployment. Still, the density of cancellous bone 32 is not uniform and can change abruptly. Even with the utmost of care and skill, it is possible that the stylet 74 or the cutting edge 90 can slide into and poke through cortical bone 28 in the anterior wall of the vertebral body 26. This can create a hole or breach B in the anterior cortical wall 28 of the vertebral body 26, as FIG. 19 shows.

Figure 20A:
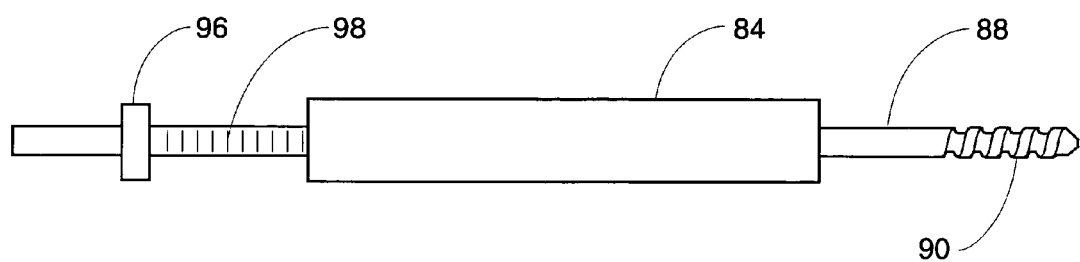
FIG. 20A is an enlarged side view of a drill bit instrument having a mechanical stop to prevent breach of an anterior cortical wall of the vertebral body.

To aid in the advancement of the cutting edge 90 through cancellous bone 32 (see FIG. 20A), the drill bit instrument 88 may include a mechanical stop 96. In use, the mechanical stop 96 abuts against the proximal end of the cannula instrument 84. The abutment stops further advancement of the drill bit instrument 88 into the interior of the vertebral body 26.

The location of the mechanical stop 96 may be adjustable, to provide variable lengths of advancement, depending upon the size of the vertebral body 26 or other bone volume targeted for treatment.

Alternatively, or in combination, the drill bit instrument 88 may include markings 98 located along its length at increments from its terminus. The markings 98 register with the exposed proximal edge of the cannula instrument 84 (see FIG. 20A), to allow the physician to remotely gauge the position of the instrument in the vertebral body 26.

Figure 20B:
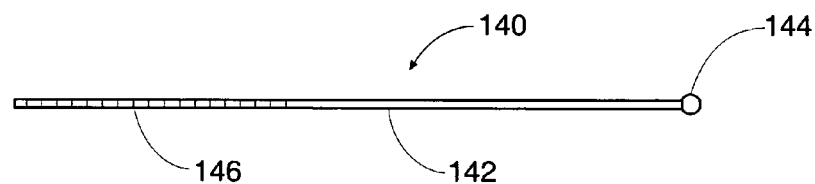
FIG. 20B is an enlarged side view of a cortical wall probe that can be deployed to gauge the interior dimensions of a vertebral body without breaching an anterior cortical wall of the vertebral body.

To aid the advancement of the stylet 74, the trocar 330, or the drill bit instrument 88 within the vertebral body, without breach of the anterior cortical wall, the physician can also make use of a cortical wall probe 140, as shown in FIG. 20B. The cortical wall probe 140 comprises a generally rigid stylet body 142 having a blunt distal tip 144, which desirably cannot easily pierce the anterior cortical wall of the vertebral body. In the illustrated embodiment, the blunt distal tip 144 comprises a rounded ball shape.

The cortical wall probe 140 can be deployed through the formed access opening before any significant penetration of cancellous bone occurs. For example, after the access opening is formed using the spinal needle assembly 70, but before the stylus 72 and stylet 74 are advanced a significant distance into cancellous bone, the stylet 74 can be withdrawn and, instead, the cortical wall probe 140 advanced through the stylus, 72. The physician advances the cortical wall probe 140 through cancellous bone, until the physician tactilely senses contact between the blunt distal tip 144 and the anterior cortical wall. Desirably, the probe 140 is radiopaque, so that its advancement through cancellous bone and its contact with the anterior cortical wall within the vertebral body can be visualized, e.g., either by x-ray or real time fluoroscopy or MRI. Using the cortical wall probe 140, the physician can gauge the distance between the access opening into the vertebral body and the anterior cortical wall, in a manner that avoids penetration of the anterior cortical wall.

The cortical wall probe 140 can carry length markings 146 on its proximal region, which, when contact with the anterior cortical wall occurs and/or is imminent, indicate the distance a subsequent instrument can be advanced down the stylus 72 (or cannula instrument 84) before contacting the anterior cortical wall. The information obtained from the cortical wall probe 140 can also be used to set the mechanical stop 96 (previously described), to physically prevent advancement of the trocar 330 or drill bit instrument 88 before contact with the anterior cortical wall occurs.

In the event of a breach or suspected breach of the anterior cortical wall of the vertebral body, the physician can alternatively utilize the cortical wall probe 140 to safely and easily determine the existence and/or extent of a wall breach. Because the distal tip 144 of the probe is blunt, the tip 144 desirably will not easily pass through an intact anterior cortical wall, which allows the physician to "tap" the tool along the inner surface of the anterior cortical wall while searching for breaches. Where a wall breach has occurred, and the tool could pass through the breach, the blunt tip 144 of the tool desirably will not pierce or damage soft tissues, such as the aorta or major veins, located forward of the cortical wall. If desired, the blunt tip 144 can alternatively be formed of a soft, deformable material such as rubber or plastic.

If a breach B occurs, a suitable material may be placed into the breach B to plug it. For example, a demineralized bone matrix material, such as GRAFTON™ material, may be used. The material can be placed, e.g., on the distal end of the obturator instrument 78 or trocar 330. The instrument 78 is deployed carrying the plugging material to the exterior side wall where the breach B occurs. The instrument 78 deposits the plugging material in the breach B, to thereby close it from the outside of the vertebral body 26.

The physician can take steps to counteract undetermined cortical wall breaches, either as may possibly preexist before cavity formation or which may possibly exist after cavity formation. Even if a breach is not known to exist, the physician can nevertheless elect to insert a suitable plug material (e.g., GRAFTON™ bone matrix material, or Collagraft™ sheet material, or a mesh-type material) into the vertebral body, either before or after the structure 56 is expanded. The presence of a plug material guards against the possibility of leaks, whether they exist or not. Furthermore, if inserted before the structure 56 is expanded, the presence of the plug material in the vertebral body can serve to make the distribution of the expansion force of the structure 56 more uniform. The presence of the plug material within the vertebral body as the structure 56 expands can also protect against protrusion of the expanding structure 56 through any preexisting breach in the cortical wall as well as any breaches created during expansion of the structure 56, or can otherwise protect weakened cortical walls during expansion of the structure 56.

4. Cannula Locking Device

Figure 26A:
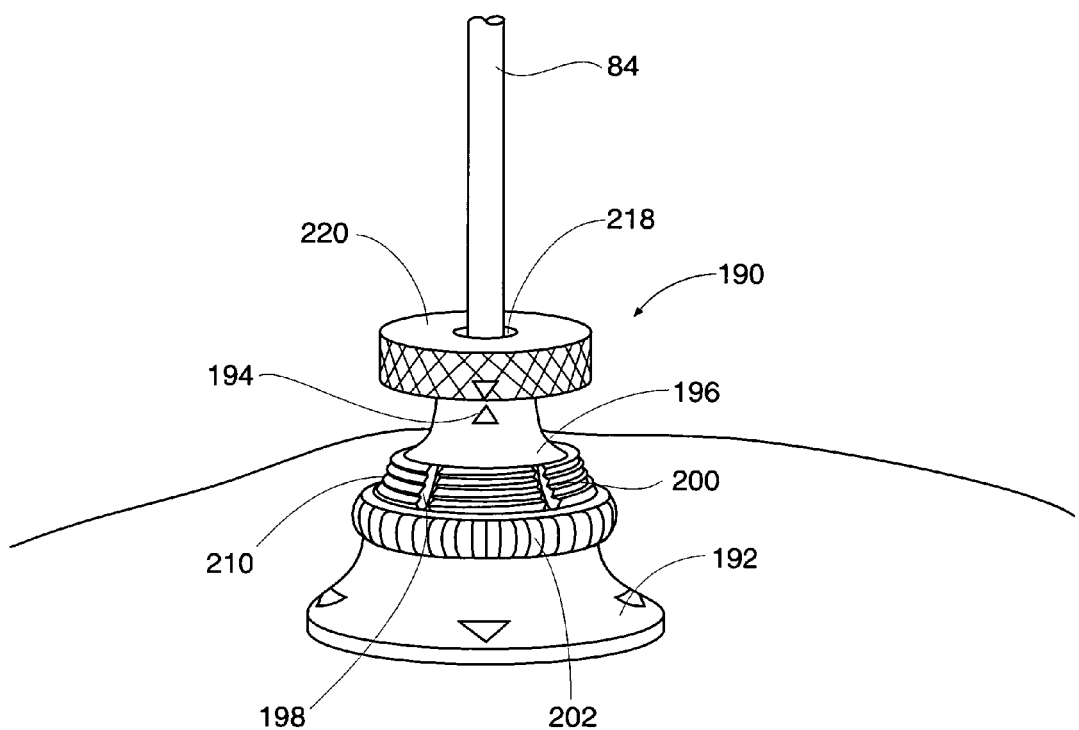
FIG. 26A is a perspective view of one embodiment of a locking device for a cannula instrument.

Referring to FIG. 26A, a cannula locking device 190 can be used to aid in stabilizing the cannula instrument 84 while accessing a vertebral body. The locking device 190 can be variously constructed.

In the embodiment shown in FIG. 26A, the locking device 190 includes a generally planar base 192. In use, the base 192 rests upon a skin surface surrounding the targeted incision site. If desired, the base 192 can incorporate an adhesive (not shown) to secure the base to the patient's skin or to other material located at or near the surgical site.

An instrument grip 194 is supported on the base 192. The instrument grip 194 includes a channel 218 which slidingly receives the cannula instrument 84, which, in this embodiment, is intended to be placed into the grip 194 distal end first. A ring 220, threaded to the grip 194, can be provided to tighten the channel 218 about the cannula instrument 84, to thereby prevent axial movement of the cannula instrument 84 within the channel 218.

The grip 194 also includes a tenon 196, which fits within a mortise 198 on the base 192. The mortise 198 and tenon 196 together form a joint 200. The grip 194 pivots 360-degrees in transverse and/or orbital paths within the joint 200.

The mortise 198 is bounded by a collet 210, about which a retaining ring 202 is threadably engaged. Twisting the ring 202 in one direction (e.g., clockwise) closes the collet 210 about the tenon 196, locking the position of the grip 194 relative to the base 192. Twisting the ring 202 in an opposite direction opens the collet 210 about the tenon 196, freeing the grip 194 for pivotal movement relative to the base 192.

To use the device 190, the physician manipulates the cannula instrument 84 held in the grip 194 into a desired axial and angular orientation. The physician thereafter locks the grip 194 (tightening the rings 202 and 220) to hold the cannula instrument 84 in the desired axial and angular orientation. The physician can manipulate and lock the cannula instrument 84 in any desired order, either before or after passage of the instrument 84 through the skin, and/or before or after passage of the instrument 84 through cortical bone, or combinations thereof. Markings 204 on the grip 194 and base 192 allow the physician to gauge movement of the grip 194 relative to the base 192 or another reference point.

The locking device 190 is preferably made from a material that is not highly radiopaque, e.g., polyurethane or polycarbonate. The device 190 will therefore not obstruct fluoroscopic or x-ray visualization of the cannula instrument 84 during use.

When locked, the device 190 prevents unintended movement of the cannula instrument 84 along the skin surface. The likelihood that the cannula instrument 84 will be bent or its position inadvertently shifted during use is thereby mitigated. The device 190 also allows the physician to remove his/her hands from the instrument 84, e.g., to allow clear fluoroscopy or x-ray visualization. The device 190 obviates the need for other types of clamps that are radiopaque or are otherwise not well suited to the task.

Figure 26B:
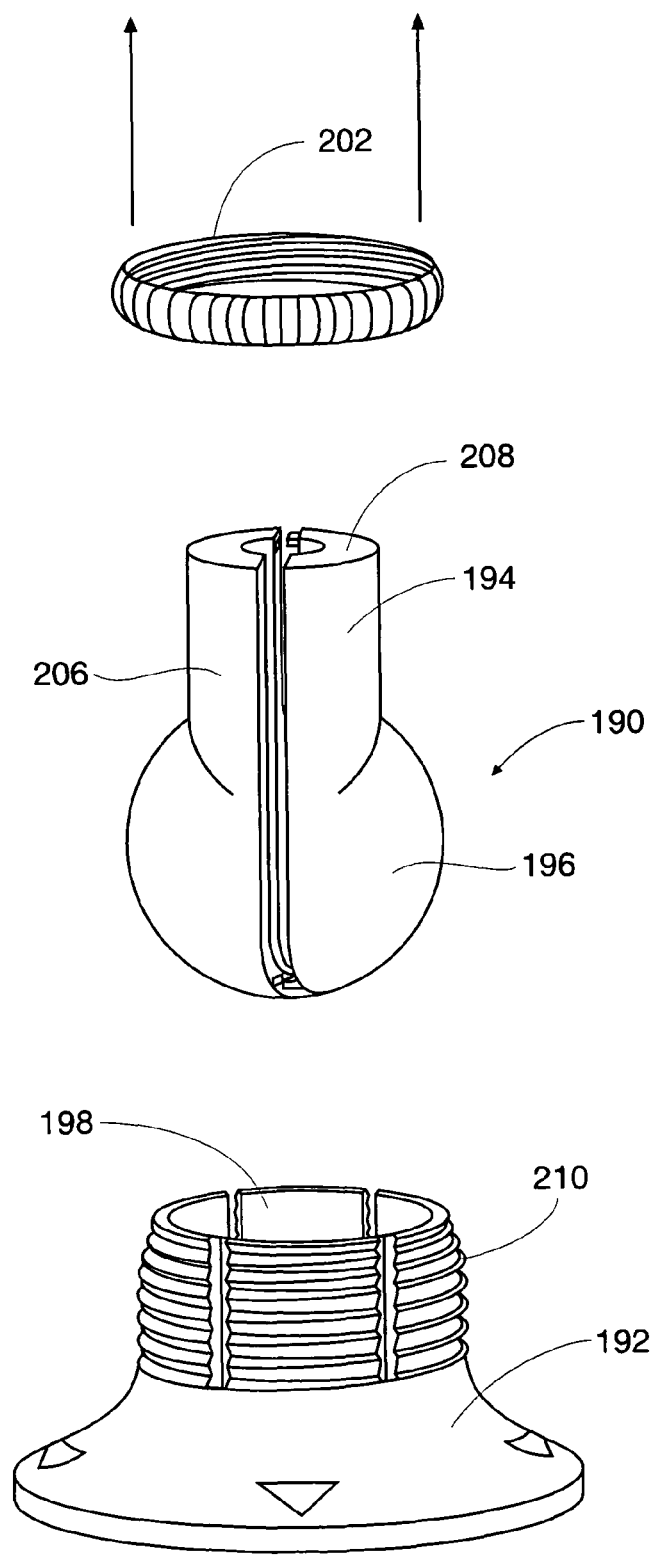
FIG. 26B is a perspective view of another embodiment of a locking device for a cannula instrument.

As FIG. 26B shows, in an alternative embodiment, the retaining ring 202 can be loosened to a point that opens the collet 210 enough to free the grip 194 from the base 192. In this arrangement, the grip 194 comprises members 206 and 208 that can be split apart when separated from the confines of the collet 210. The cannula instrument 84 can be captured between the spit-apart members 206 and 208 as they are fitted back together, obviating the need to load the cannula instrument 84 distal end first in the grip 194.

When fitted together, the tenon 196 can be returned to the mortise 198. The retaining ring 202 can be tightened sufficiently to close the collet 210 about the tenon 196, forming the joint 200. Further tightening of the retaining ring 202 about the mortise 198 closes the joint 200 (as before described), locking the grip 194 a desired orientation relative to the base 192. Subsequent loosening of the retaining ring 202 permits separation of the grip 194 from the base 192, so that the members 206 and 208 can be split apart to free the cannula instrument 84. In one, embodiment, the grip 194 can contact the cannula directly, such that the cannula is substantially "locked" in position when the grip 194 is compressed against the cannula. In an alternate embodiment, an O-ring (not shown) can be located within the grip 194, such that compression of the grip causes the O-ring to push against the cannula, desirably substantially "locking" the cannula in position within the grip 194.

B. Forming the Cavities

Figure 16F:
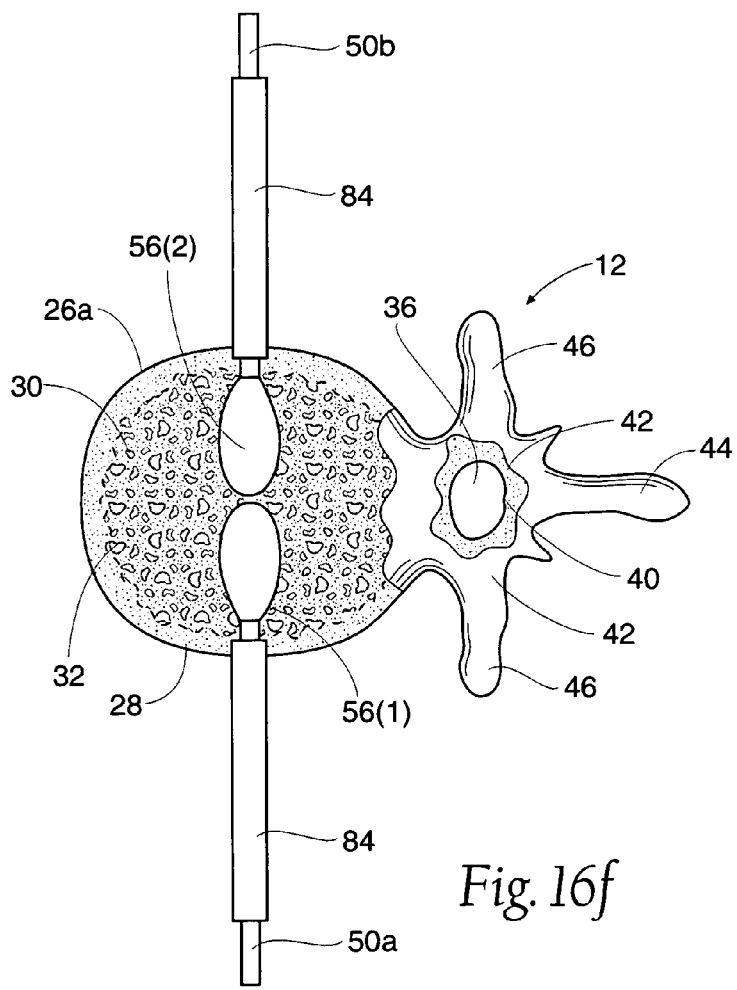

Once the accesses PLA have been formed, the physician advances individual catheter tubes 50 through the cannula instrument 84 and passage of each access, into the interior volume of the associated vertebral body 26A, 26B, and 26C. FIG. 16F shows this deployment in vertebral body 26A.

The expandable structures 56(1) to 56(6) are then expanded in the alternating, step wise fashion as already described. The compression forms the interior cavity 64 in each vertebral body 26A, 26B, and 26C.

As FIGS. 4 and 5 show; the expandable structure 56 can carry at least one radiopaque marker 102, to enable remote visualization of its position within the vertebral body 26. In the illustrated embodiment, the expandable structure 56 carries a radiopaque marker 102 on both its distal and proximal end.

As before described, when fluoroscopic or CT visualization is used to monitor expansion of the structure 56, the fluid used to cause expansion of the structure 56 is preferably rendered radiopaque (e.g., using Renografin™ material). The visualization instrument (e.g., a C-arm fluoroscope) is typically positioned on the operating table to view laterally along one side of the spinal column. The presence of radiopaque expansion medium in a expanded structure 56 in the vertebral body 26 can block effective visualization elsewhere in the vertebral body, e.g., where cavity formation using another structure 56 or where vertebroplasty or another form of treatment is intended to occur.

Visualization can be facilitated under these circumstances by removal or dilution of the radiopaque medium within the structure 56 after the structure is expanded to create a cavity.

In one embodiment (see FIG. 32), an exchange chamber 400 is provided, which is divided into two compartments 402 and 404 by a piston 414 that is movable by pressure upon a plunger 420. Dual lumens 406 and 408 communicate with the interior of the structure 56. The lumen 406 communicates with the source 422 of radiopaque medium 410 to convey the medium 410 into the structure 56 to cause expansion and cavity formation in the first instance. The lumen 406 also communicates with the compartment 402 on one side of the piston 414.

The other compartment 404 of the chamber 400 contains a replacement expansion medium 412. The replacement medium 412 is free of a radiopaque material or, if desired, can contain a partially-radiopaque material. The lumen 408 communicates with this compartment 404.

After expansion of the structure 56 with the radiopaque medium 410, movement of the piston 414 will draw the radiopaque medium 410 from the structure 56 (through lumen 402). Simultaneously, the piston 414 will displace the radiopaque-free medium 412 into the structure 56 (through lumen 404). Piston movement exchanges the radiopaque medium 410 with the radiopaque-free medium 412, without collapsing the structure 56.

In an alternative embodiment, an ion exchange material for the radiopaque material in the medium 410 (e.g., iodine) can be introduced into the radiopaque medium 410 contained within the structure 56. The ion exchange material selectively binds the radiopaque material, diluting the radiopaque qualities of the medium 410. The radiopaque medium 410 can be circulated through an ionic exchange chamber outside the structure 56, or the ion exchange material can be introduced into the structure 56 through an interior lumen within the structure 56 itself.

Alternatively, a material that causes precipitation of radiopaque material can be introduced into the radiopaque medium 410 within the structure 56 (e.g., through an interior lumen). The precipitation selectively causes the radiopaque material to settle downward within the structure 56, out of the lateral visualization path, thereby diluting the radiopaque qualities of the medium 410.

As FIG. 5 shows, the expandable structure 56 can also include an interior tube 104. The interior tube 104, contains an interior lumen 106 that passes through the expandable structure 56.

The interior lumen 106 can be used to convey a flowable material or liquid, e.g. saline or sterile water, to flush materials free of the distal region of the structure 56, when in use. The interior lumen 106 can also be used to aspirate liquid material from the interior of the vertebral body 26 as the procedure is performed. The interior lumen 106 can also be used to introduce a thrombogenic material, e.g., a clotting agent, into contact with cancellous bone 32 during the procedure. The expandable structure 56 itself can be also dipped into thrombin prior to its introduction into the vertebral body 26 to facilitate in situ coagulation.

The interior lumen 106 can also be sized to receive a stiffening member or stylet 108 (see FIG. 5). The stylet 108 keeps the structure 56 in a desired distally straightened condition during its passage through the cannula instrument 84. Once the structure 56 is located in the desired location within cancellous bone, the physician can remove the stylet 108, and thereby open the interior lumen, 106 for conveyance of liquids to and from cancellous bone, as just described.

The stylet 108 can also have a preformed memory, to normally bend its distal region. The memory is overcome to straighten the stylet 108 when passed through the cannula instrument 84. However, as the structure 56 and stylet 108 advance free of the cannula instrument 84, passing into cancellous bone 32, the preformed memory bends the stylet 108. The bent stylet 108 shifts the axis of the structure relative to the axis of the access path PLA. The prebent stylet 108, positioned within the interior of the structure 56, aids in altering the geometry of the structure 56 to achieve a desired orientation when deployed for use.

If the stylet 108 is comprised of a shape memory alloy, such as nickel-titanium (Nitinol), copper or iron based alloys, the distal end of the stylet 108 can, be set to a prebent "parent shape," and then subsequently bent to a substantially straight shape for introduction into the vertebral body. When the stylet 108 is in its desired position, and bending of the distal end is desired, heat can be applied to the proximal end of the stylet 108, which desirably will cause the distal end of the stylet 108 to assume its parent shape in a known manner. Alternatively, the stylet 108 can be comprised of a shape memory allowing material having a transition temperature at or below human body temperature. Such a stylet 108 can be cooled prior to and/or during introduction into the human body, and once in the proper position, the cooling source can be removed, and the patient's body heat will cause the stylet 108 to assume its pre-bent parent shape. If desired, the stylet can be initially positioned within the vertebral body, with the distal end deflecting within the cancellous bone, or the distal end can be deflected during insertion into the vertebral body.

Figure 25:
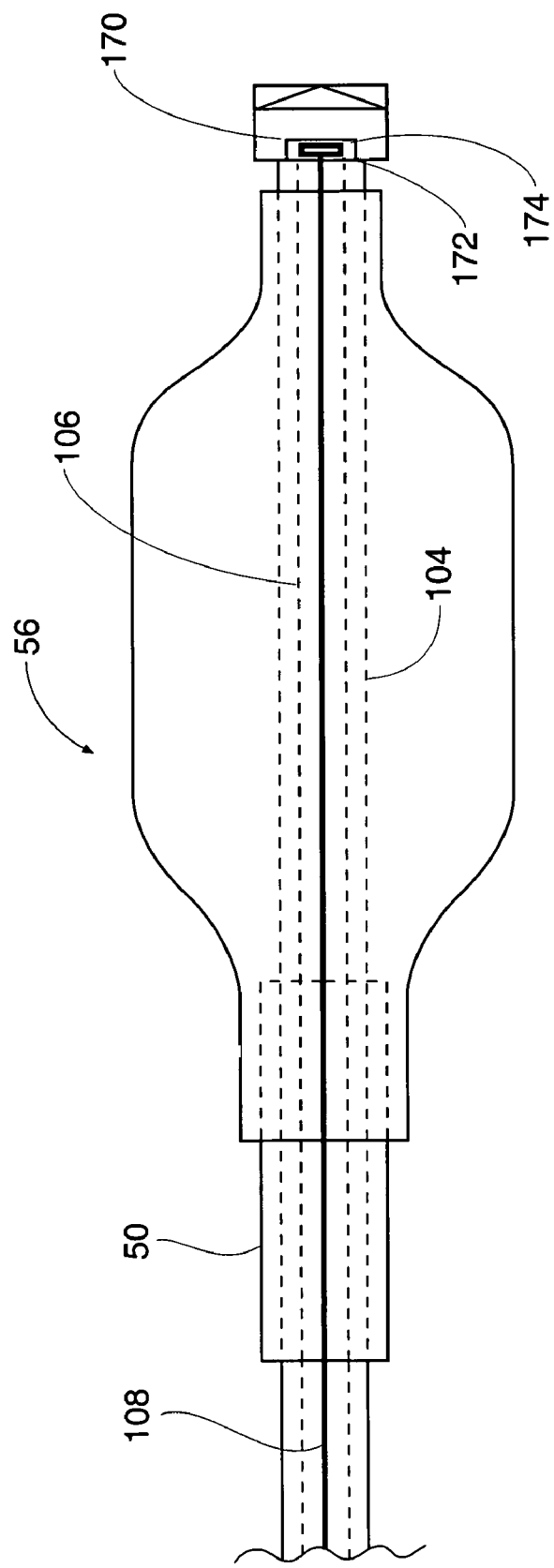
FIG. 25 is an enlarged side section view of an expandable body carried at the end of a catheter tube, which further includes an integrated drill bit instrument.

As FIG. 25 shows, the catheter tube 50 can itself carry a drill bit element 170. The drill bit element 170 may be variously constructed. As shown in FIG. 25, the drill bit element 170 comprises a metal cutting cap bonded or otherwise mounted on the distal end of the interior catheter tube 104, beyond the expandable structure 56. In this arrangement, the stylet 108 can include a keyed distal end 172, which mates within an internal key way 174 in the drill bit element 170. The stylet 108 thereby serves to stiffen the distal end of the catheter tube 104, so that torsional and compressive loads can be applied to the drill bit element 170. Alternatively, the interior structure of the catheter tube 104 can be otherwise reinforced to transmit torsional and compressive load forces to the drill bit element 170. Using the drill bit element 170, the physician can open an access opening in the cortical bone, without use of the separate drill bit instrument 88.

1. Desired Physical and Mechanical Properties for the Expandable Structure

The material from which the structure 56 is made should possess various physical and mechanical properties to optimize its functional capabilities to compact cancellous bone. Important properties are the ability to expand its volume; the ability to deform in a desired way when expanding and assume a desired shape inside bone; and the ability to withstand abrasion, tearing, and puncture when in contact with cancellous bone.

2. Expansion Property

A first desired property for the structure material is the ability to expand or otherwise increase its volume without failure. This property enables the structure 56 to be deployed in a collapsed, low profile condition subcutaneously, e.g., through a cannula, into the targeted bone region. This property also enables the expansion of the structure 56 inside the targeted bone region to press against and compress surrounding cancellous bone, or move cortical bone to a prefracture or other desired condition, or both.

The desired expansion property for the structure material can be characterized in one way by ultimate elongation properties, which indicate the degree of expansion that the material can accommodate prior to failure. Sufficient ultimate elongation permits the structure 56 to compact cortical bone, as well as lift contiguous cortical bone, if necessary, prior to wall failure. Desirably, the structure 56 will comprise material able to undergo an ultimate elongation of at least 50%, prior to wall failure. when expanded outside of bone. More desirably, the structure will comprise material able to undergo an ultimate elongation of at least 150%, prior to wall failure, when expanded outside of bone. Most desirably, the structure will comprise material able to undergo an ultimate elongation of at least 300%, prior to wall failure, when expanded outside of bone.

Alternatively, the structure 56 can comprise one or more non-compliant or partially compliant materials having substantially lower ultimate elongation properties, including, but not limited to, kevlar, aluminum, nylon, polyethylene, polyethylene-terephthalate (PET) or mylar. Such a structure would desirably be initially formed to a desired shape and volume, and then contracted to a collapsed, lower profile condition for introduction through a cannula into the targeted bone region. The structure could then be expanded to the desired shape and volume to press against and compress surrounding cancellous bone and/or move cortical bone to a prefracture or desired condition, or both. As another alternative, the structure could comprise a combination of non-compliant, partially compliant and/or compliant materials.

3. Shape Property

A second desired property for the material of the structure 56, either alone or in combination with the other described properties, is the ability to predictably deform during expansion, so that the structure 56 consistently achieves a desired shape inside bone.

The shape of the structure 56, when expanded in bone, is desirably selected by the physician, taking into account the morphology and geometry of the site to be treated. The shape of the cancellous bone to be compressed and/or cortical bone to be displaced, and the local structures that could be harmed if bone were moved inappropriately, are generally understood by medical professionals using textbooks of human skeletal anatomy along with their knowledge of the site and its disease or injury, and also taking into account the teachings of U.S. patent application Ser. No. 08/788,786, filed Jan. 23, 1997, and entitled "Improved Inflatable Device for Use in Surgical Protocol Relating to Fixation of Bone," which is incorporated herein by reference. The physician is also desirably able to select the desired expanded shape inside bone based upon prior analysis of the morphology of the targeted bone using, for example, plain film x-ray, fluoroscopic x-ray, or MRI or CT scanning.

Where compression of cancellous bone and/or cavity creation is desired, the expanded shape inside bone is selected to optimize the formation of a cavity that, when filled with a selected material, provides support across the region of the bone being treated. The selected expanded shape is made by evaluation of the predicted deformation that will occur with increased volume due to the shape and physiology of the targeted bone region.

Where displacement of cortical bone is desired, the expanded shape can be chosen to maximize the amount of force the structure exerts on cortical bone, maximize force distribution over the largest possible surface area of the cortical bone and/or maximize displacement of the cortical bone in one or more desired directions. Alternatively, the structure can be designed to impart a maximum force on a specific area of the cortical bone so as to cause desired fracture and/or maximum displacement of specific cortical bone regions.

To aid in selecting a suitable size for the expandable structure 56, the trocar 330 of the composite instrument 310 (see FIGS. 27 and 28) can carry an array of grooves or like markings 380, which can be viewed under fluoroscopic visualization. The markings 380 allow the physician to estimate the distance across the vertebral body, thereby making it possible to estimate the desired size of the expandable structure 56. Because the cannula instrument 84 is a relatively thin-walled structure, and the trocar 330 is a relatively thicker solid structure, the physician is able to visualize the markings 380 by fluoroscopy, even when the markings 380 are inside the cannula instrument 84.

In some instances, it is desirable, when creating a cavity, to also move or displace the cortical bone to achieve the desired therapeutic result. Such movement is not per se harmful, as that term is used in this Specification, because it is indicated to achieve the desired therapeutic result. By definition, harm results when expansion of the structure 56 results in a, worsening of the overall condition of the bone and surrounding anatomic structures, for example, by injury to surrounding tissue or causing a permanent adverse change in bone biomechanics.

If desired, the structure 56 can be used to generate sufficient force to fracture cortical bone and position the fractured cortical bone in a new orientation and/or into a more desired position. Where the bone has fractured and/or compressed in the past, and subsequently healed, the present methods and devices can be utilized to safely reposition the cortical bone to a more desired position. For example, where a vertebral compression fracture has healed in a depressed and/or fractured position, the disclosed devices and methods can be utilized to re-fracture and reposition the fractured bone to a more desirable position and/or orientation. By generating sufficient force to fracture the bone from the interior, through expansion of an expandable body, only a single access portal through the cortical bone need be formed.

If desired, the structure could alternatively be used in conjunction with various devices, including but not limited to lasers, drills, chisels or sonic generators (e.g. lithotripers), these devices being used to selectively weaken and/or fracture cortical bone along desired lines and/or in a desired manner. Once the targeted cortical bone is sufficiently weakened, the structure 56 can be used to fracture the bone and/or reposition the cortical bone to a new orientation and/or into a more desired position.

In a similar manner, the structure 56 can be used to fracture and reposition a portion of the cortical bone, such as where the bone has grown and/or healed in a deformed condition. For example, in a patient having severe scoliosis (e.g., osteopathic scoliosis), the vertebral column may be laterally curved due to bone deformation. The present methods and devices can be utilized to safely fracture and/or reposition the cortical bone to a more desired position. If desired, sections of the bone can be scored, weakened and/or pre-fractured by various devices including, but not limited to, sharp knives, saws, awls, drills, lasers and/or lithotripters, creating desired lines along which the bone will tend to fracture. The depressed sections of the vertebral body can desirably be elevated and reinforced, thereby reducing the lateral curve of the vertebral column and preventing further lateral deformation of the spine. By fracturing and/or displacing only a portion of the cortical bone, the present methods and devices minimize unnecessary muscular-skeletal trauma while permitting treatment of the disease.

As one general consideration, in cases where the bone disease causing fracture (or the risk of fracture) is the loss of cancellous bone mass (as in osteoporosis), the selection of the expanded shape of the structure 56 inside bone should take into account the cancellous bone volume which should be compacted to achieve the desired therapeutic result. An exemplary range is about 30% to 90% of the cancellous bone volume, but the range can vary depending upon the targeted bone region. Generally speaking, compacting less of the cancellous bone volume leaves more uncompacted, diseased cancellous bone at the treatment site.

Another general guideline for the selection of the expanded shape of the structure 56 inside bone is the amount that the targeted fractured bone region has been displaced or depressed. The expansion of the structure 56 inside a bone can elevate or push the fractured cortical wall back to or near its anatomic position occupied before fracture occurred. Where the structure 56 directly contacts the depressed cortical bone, and elevates the cortical bone through direct contact with the expanding structure, compaction of cancellous bone may not be necessary or desired.

For practical reasons, it is desired that the expanded shape of the structure 56 inside bone, when in contact with cancellous bone, substantially conforms to the shape of the structure 56 outside bone, when in an open air environment. This allows the physician to select in an open air environment a structure having an expanded shape desired to meet the targeted therapeutic result, with the confidence that the expanded shape inside bone will be similar in important respects.

In some instances, it may not be necessary or desired for the structure to predictably deform and/or assume a desired shape during expansion inside bone. Rather, it may be preferred that the structure expand in a substantially uncontrolled manner, rather than being constrained in its expansion. For example, where compaction of weaker sections of the cancellous bone is desired, it may be preferred that the structure initially expand towards weaker areas within the bone. In such cases, the structure can be formed without the previously-described shape and/or size, and the expanded shape and/or size of the structure can be predominantly determined by the morphology and geometry of the treated bone.

An optimal degree of shaping can be achieved by material selection and by special manufacturing techniques, e.g., thermoforming or blow molding, as will be described in greater detail later.

4. Toughness Property

A third desired property for the structure 56, either alone or in combination with one or more of the other described properties, is the ability to resist surface abrasion, tearing, and puncture when in contact with cancellous bone. This property can be characterized in various ways.

One way of measuring a material's resistance to abrasion, tearing and/or puncture is by a Taber Abrasion test. A Taber Abrasion test evaluates the resistance of a material to abrasive wear. For example, in a Taber Abrasion test configured with an H-18 abrasive wheel and a 1 kg load for 1000 cycles (ASTM Test Method D 3489), Texin® 5270 material exhibits a Taber Abrasion value of approximately 75 mg loss. As another example, under the same conditions Texin® 5286 material exhibits a Taber Abrasion value of approximately 30 mg loss. Typically, a lower Taber Abrasion value indicates a greater resistance to abrasion. Desirably, one embodiment of an expandable structure will comprise material having a Taber Abrasion value under these conditions of less than approximately 200 mg loss. More desirably, the structure will comprise material having a Taber Abrasion value under these conditions of less than approximately 145 mg loss. Most desirably, the structure will comprise material having a Taber Abrasion value under these conditions of less than approximately 90 mg loss. Of course, materials having a Taber Abrasion value of greater than or equal to 200 mg loss may be, utilized to accomplish some or all of the objectives of the present invention.

Another way of measuring a material's resistance to abrasion, tearing and/or puncture is by Elmendorf Tear Strength. For example, under ASTM Test Method D 624, Texin® 5270 material exhibits a Tear Strength of 1,100 lb-ft/in. As another example, under the same conditions, Texin 5286 exhibits a Tear Strength of 500 lb-ft/in. Typically, a higher Tear Strength indicates a greater resistance to tearing. Desirably, an alternative embodiment of an expandable structure will comprise material having a Tear Strength under these conditions of at least approximately 150 lb-ft/in. More desirably, the structure will comprise material having a Tear Strength under these conditions of at least approximately 220 lb-ft/in. Most desirably, the structure will comprise material having a Tear Strength under these conditions of at least approximately 280 lb-ft/in. Of course, materials having a Tear Strength of less than or equal to 150 lb-ft/in may be utilized to accomplish some or all of the objectives of the present invention.

Another way of measuring a material's resistance to abrasion, tearing and/or puncture is by Shore Hardness. For example, under ASTM Test Method D 2240, Texin® 5270 material exhibits a Shore Hardness of 70 D. As another example, under the same conditions, Texin® 5286 material exhibits a Shore Hardness of 86A. Typically, a lower Shore Hardness number on a given scale indicates a greater degree of elasticity, flexibility and ductility. Desirably, another alternative embodiment of an expandable structure will comprise material having a Shore Hardness under these conditions of less than approximately 75 D. More desirably, the structure will comprise material having a Shore Hardness under these conditions of less than approximately 65 D. Most desirably, the structure will comprise material having a Shore Hardness under these conditions of less than approximately 100 A. Of course, materials having a Shore Hardness of greater than or equal to 75 D may be utilized to accomplish some or all of the objectives of the present invention.

It should also be noted that another alternative embodiment of a expandable structure incorporating a plurality of materials, such as layered materials and/or composites, may possess significant resistance to surface abrasion, tearing and puncture. For example, a layered expandable structure incorporating an inner body formed of material having a Taber Abrasion value of greater than 200 mg loss and an outer body having a shore hardness of greater than 75 D might possess significant resistance to surface abrasion, tearing and puncture. Similarly, other combinations of materials could possess the desired toughness to accomplish the desired goal of compressing cancellous bone and/or moving cortical bone prior to material failure.

5. Creating a Pre-Formed Structure

The expansion and shape properties just described can be enhanced and further optimized for compacting cancellous bone by, selecting an elastomer material, which also possess the capability of being preformed (i.e., to acquire a desired shape by exposure, e.g., to heat and pressure), e.g., through the use of conventional thermoforming or blow molding techniques. Candidate materials that meet this criteria include polyurethane, silicone, thermoplastic rubber, nylon, and thermoplastic elastomer materials.

In the illustrated embodiment, TEXIN® 5286 polyurethane material is used. This material is commercially available from Bayer in pellet form. The pellets can be processed and extruded in a tubular shape. The structure 56 can be formed by exposing a cut length of the tubular extrusion to heat and then enclosing the heated tube within a mold while positive interior pressure is applied to the tube length 60, such as in a conventional balloon forming machine.

Further details regarding the creation of the expandable structure 56 can be found in copending U.S. patent application Ser. No. 09/420,529, filed Oct. 19, 1999, and entitled "Expandable Preformed Structures For Deployment in Interior Body. Regions", which is incorporated herein by reference.

6. Saline Infusion

In the treatment of crush, compression, or depression fracture, the expandable structure 56 serves to move cortical bone 28 back to its original or proper anatomic condition. This result can be achieved as the cavity is formed, by expansion of the structure 56 within cancellous bone 32 to physically move surrounding compressed or depressed cortical bone 28. Alternatively, as previously described, the cortical bone can be displaced through direct contact with the expanding structure.

It has been discovered that a localized vacuum condition may be created within the cavity 64 in response to the deflation and removal of the structure 56. The vacuum may abruptly move surrounding cortical bone 28, causing pain. The movement of bone after formation of the cavity 64 can also take back some of the distance the cortical bone 28 has been displaced as a result of expanding the structure 56 to form the cavity 64 in the first place. In a vertebral body 26, the vacuum can prevent full restoration of the vertebral body height.

Figure 21:
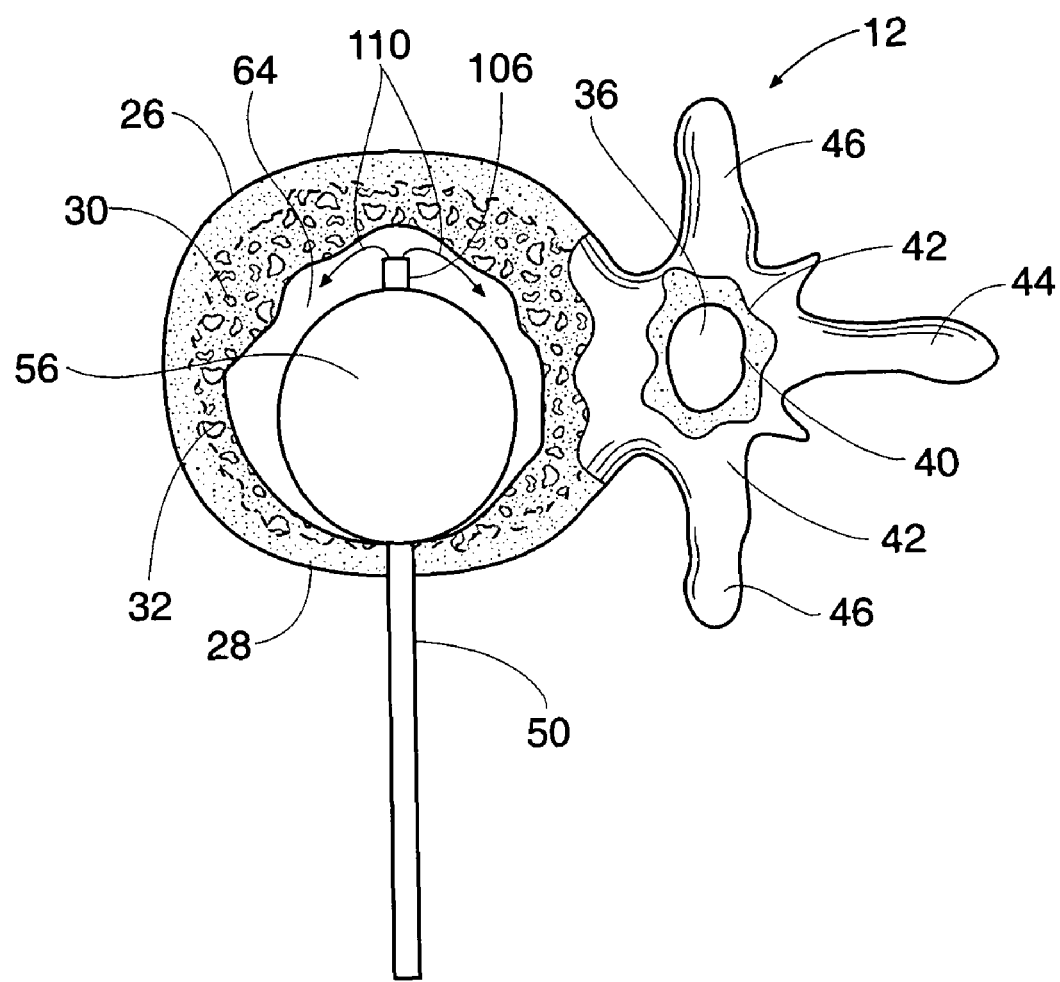
FIG. 21 is coronal view of a vertebral body with an expandable structure deployed and expanded, showing the introduction of a liquid to prevent formation of a vacuum upon the subsequent deflation and removal of the structure.

As FIG. 21 shows, to prevent formation of the vacuum, a flowable material or sterile liquid 110, e.g., saline or radiopaque contrast medium, can be introduced into the cavity 64 before and during deflation of the structure 56 and its removal from the cavity 64. The volume of liquid 110 introduced into the cavity 64 at this time is not critical, except that it should be sufficient to prevent the formation of a significant vacuum. For example, a volume of saline equal to or greater than the volume of the cavity will typically prevent significant vacuum formation. Alternatively, volumes of saline less than the volume of the cavity can also prevent significant vacuum formation to varying degrees.

The liquid 110 can be introduced through the interior lumen 106 passing through the structure 56, as previously described. Alternatively, a small exterior tube can be carried along the catheter tube 50 or inserted separately through the cannula instrument 84 to convey vacuum-preventing liquid 110 into the cavity 64.

Alternatively, air can be used to prevent vacuum formation. Once pressure used to expand the structure 56 is released, air can pass through the interior lumen 106 to replace the volume occupied by the collapsing structure 56. If the rate of air flow through the interior lumen 106 under ambient pressure is not sufficient to replace the volume as it is formed, the air flow rate can be augmented by use of a pump.

C. Filling the Cavities

Figure 16G:
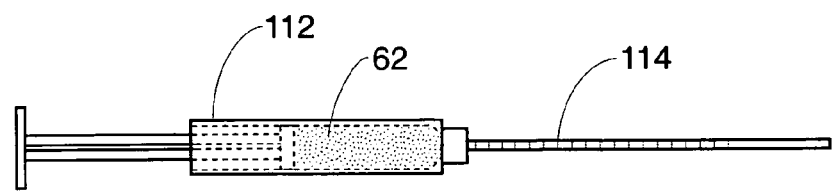

Upon formation of the cavities 64 (see FIG. 16G), the physician fills a syringe 112 with the desired volume of filling material 62, a batch of which has been previously prepared. When using an expandable structure 56 having a preformed configuration, the cavity volume created is known. The physician thereby knows the desired volume of material 62 to place in the syringe 112 for each cavity portion 64A and 64B formed in the vertebral body 26.

The physician attaches a nozzle 114 to the filled syringe 112. The physician then proceeds to deflate and remove the expandable structures 56(1) to 56(6) through the associated cannula instrument 84, in the sequential fashion already described, and to fill the associated cavity portion 64A/64B with the material 62.

Figure 16H:
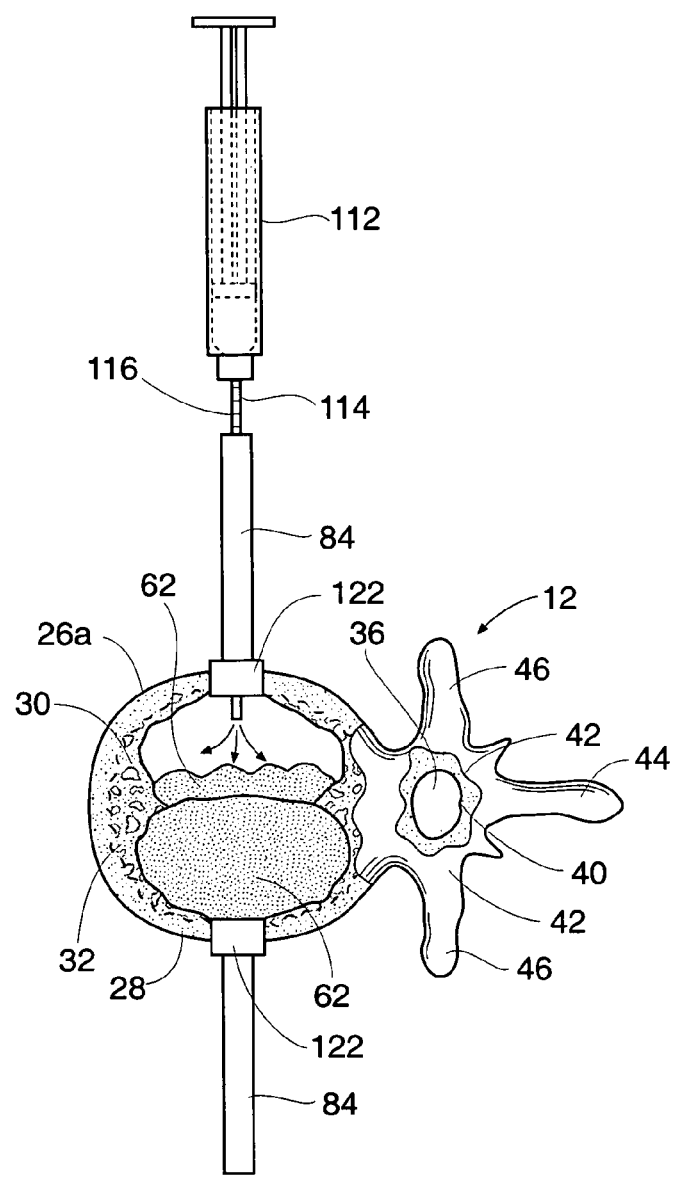
Figure 22A:
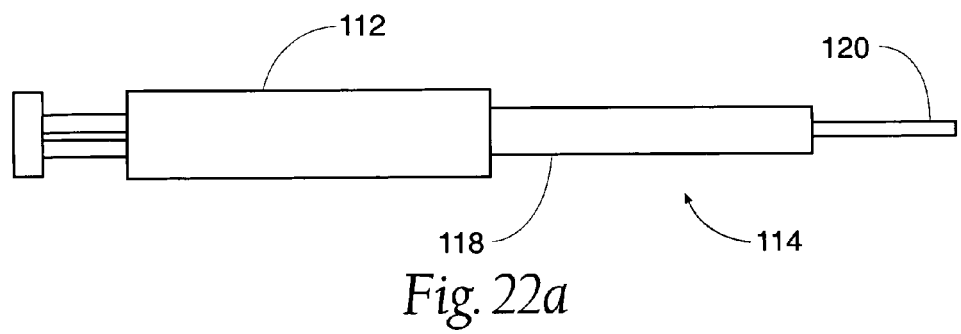
FIG. 22A is a side view of a tool to introduce material into a cavity formed in cancellous bone, with a nozzle having a stepped profile to reduce overall fluid resistance.
Figure 22B:
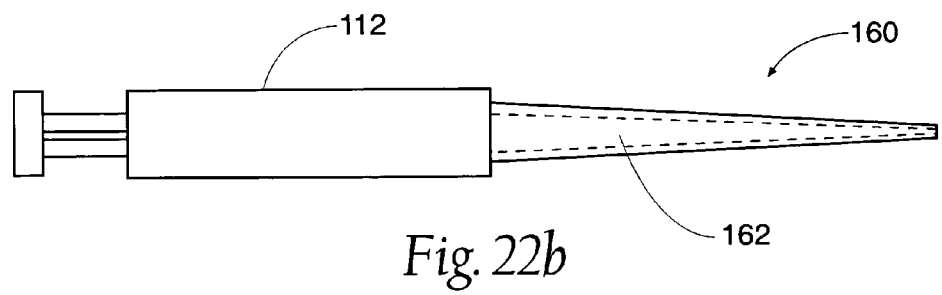
FIG. 22B is a side view of a tool to introduce material into a cavity formed in cancellous bone, with a nozzle having a tapered profile to reduce overall fluid resistance.
Figure 22C:
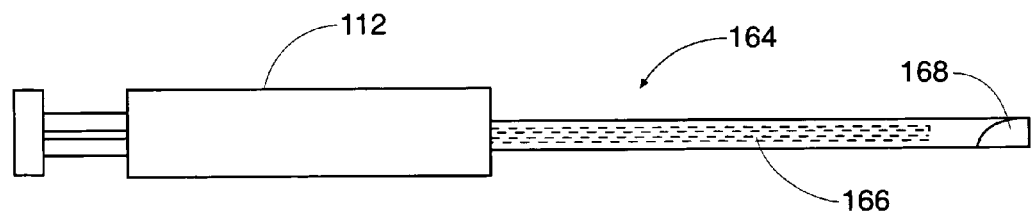
FIG. 22C is a side view of a tool to introduce material into a cavity formed in cancellous bone, with a nozzle having a reduced interior profile to reduce overall fluid resistance.

To fill a given cavity portion 64A/64B (see FIG. 16H), the physician inserts the nozzle 114 through the associated cannula instrument a selected distance into the cavity portion, guided, e.g., by exterior markings 116 or by real-time fluoroscope or x-ray or MRI visualization. The physician operates the syringe 112 to cause the material 62 to flow through and out of the nozzle 114 and into the cavity portion. As FIG. 16H shows, the nozzle 114 may posses a uniform interior diameter, sized to present a distal end dimension that facilitates insertion into the vertebral body. To reduce the overall flow resistance, however, the nozzle 114 can possess an interior diameter (e.g., see FIG. 22A) that steps down from a larger diameter at its proximal region 118 to a smaller diameter near its distal end 120. This reduces the average interior diameter of the nozzle 114 to thereby reduce the overall flow resistance. Reduced flow resistance permits more viscous material to be conveyed into the vertebral body. The more viscous material is desirable, because it has less tendency to exude from the bone compared to less viscous materials. In addition to the embodiment shown in FIG. 22A, various other constructions are possible to create a reduced diameter nozzle or tool for introducing material into bone. For example, as shown in FIG. 22B, a tool 160 can possess an interior lumen 162 that gradually tapers from a larger interior diameter to a smaller interior diameter. Or, as shown in FIG. 22C, a tool 164 can possess an interior lumen 166 that steps from a larger to a smaller interior diameter. An associated cannula instrument 168 (see FIG. 22C) may also include a reduced diameter passage, which is downsized to accommodate the reduced diameter tool and to present less flow resistance to filling material conveyed through the cannula instrument.

The reduced diameter tool may also be used in association with a vertebroplasty procedure, which injects cement under pressure into a vertebral body, without prior formation of a cavity, as will be described later.

The filling material 62 may contain a predetermined amount of a radiopaque material, e.g., barium or tungsten, sufficient to enable visualization of the flow of material 62 into the cavity portion. The amount of radiopaque material (by weight) is desirably at least 10%, more desirably at least 20%, and most desirably at least 30%. The physician can thereby visualize the cavity filling process.

As material 62 fills the cavity portion, the physician withdraws the nozzle 114 from the cavity portion and into the cannula instrument 84. The cannula instrument 84 channels the material flow toward the cavity portion. The material flows in a stream into the cavity portion.

As FIG. 16H shows, a gasket 122 may be provided about the cannula instrument 84 to seal about the access passage PLA. The gasket 122 serves to prevent leakage of the material about the cannula instrument 84.

The physician operates the syringe 112 to expel the material 62 through the nozzle 114, first into the cavity portion and then into the cannula instrument 84. Typically, at the end of the syringe injection process, material 62 should extend from the cavity and occupy about 40% to 50% of the cannula instrument 84. Alternatively, the physician can utilize the syringe 112 to fill the lumen of the nozzle 114 and/or cannula instrument 84 with material 62, and then utilize a tamping instrument 124 to expel the material from the lumen into the vertebral body.

When a desired volume of material 62 is expelled from the syringe 112, the physician withdraws the nozzle 114 from the cannula instrument 84. The physician may first rotate the syringe 112 and nozzle 114, to break loose the material 62 in the nozzle 114 from the ejected bolus of material 62 occupying the cannula instrument 84.

Figure 16I:
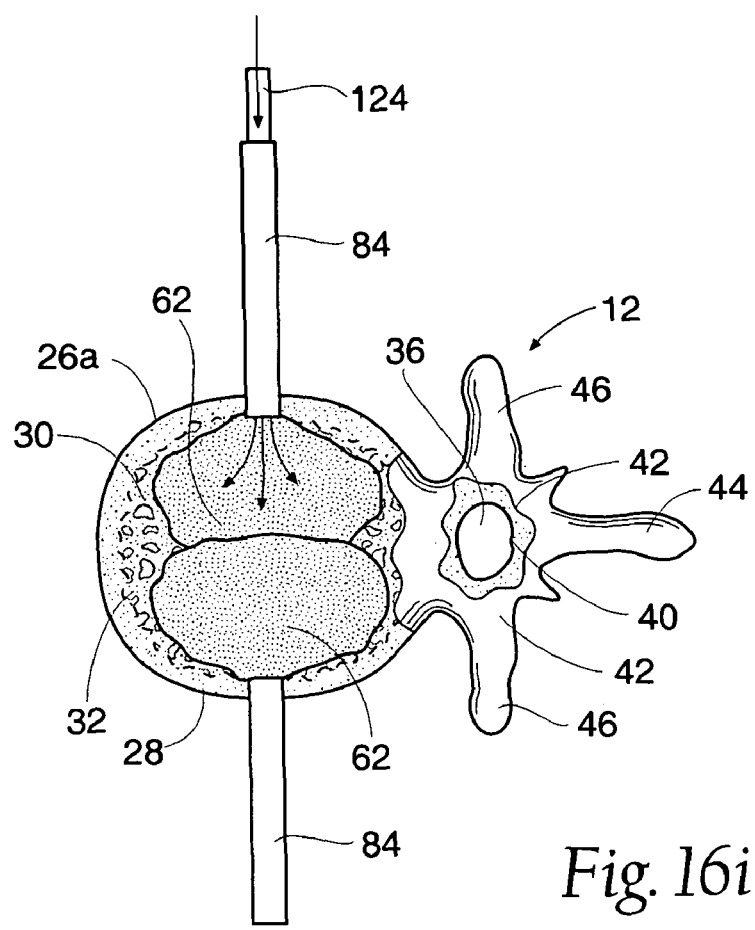

As FIG. 16I shows, the physician next advances a tamping instrument 124 through the cannula instrument 84. The distal end of the tamping instrument 124 contacts the residual volume of material 62 in the cannula instrument 84. Advancement of the tamping instrument 124 displaces progressively more of the residual material 62 from the cannula instrument 84, forcing it into the cavity portion. The flow of material 62 into the cavity portion, propelled by the advancement of the tamping instrument 124 in the cannula instrument 84, serves to uniformly distribute and compact the material 62 inside the cavity portion, into other cavities and/or openings within the bone, and into fracture lines, without the application of extremely high pressure.

The use of the syringe 112, nozzle 114, and the tamping instrument 124 allows the physician to exert precise control when filling the cavity portion with material 62. The physician can immediately adjust the volume and rate of delivery according to the particular local physiological conditions encountered. The application of low pressure, which is uniformly applied by the syringe 112 and the tamping instrument 124, allows the physician to respond to fill volume and flow resistance conditions in a virtually instantaneous fashion. The chance of overfilling and leakage of material 62 outside the cavity portion is significantly reduced.

Figure 32:
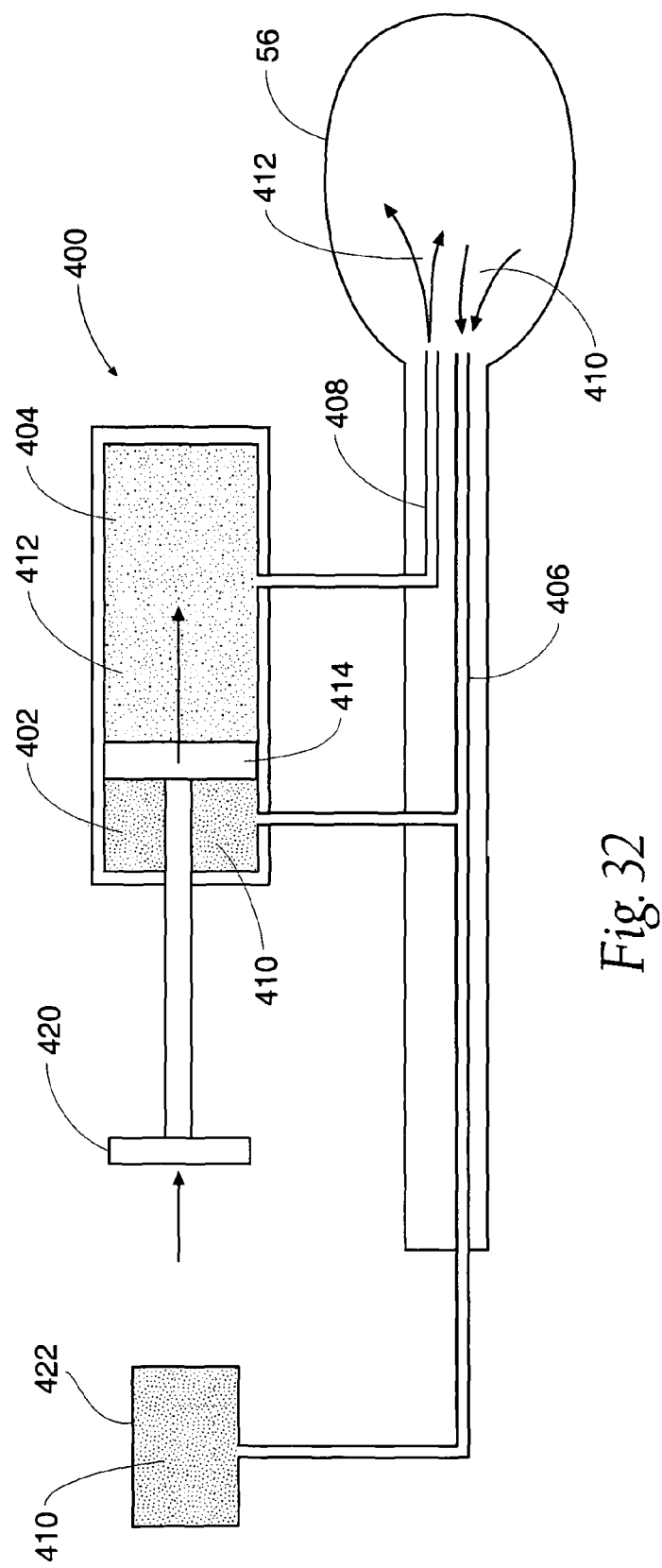
FIG. 32 depicts an exchange chamber for replacing and/or diluting the radiopaque medium within a structure with a partially-radiopaque or radiopaque-free medium.

Moreover, the tamping instrument 124 will desirably permit highly-controlled injection of material 62 under higher injection pressures as well. For example, FIG. 32 depicts a material injection instrument 500 comprising a reduced diameter nozzle 180 and a stylet 182. The stylet 182 is desirably sized to pass through the reduced diameter nozzle 180. In turn, the nozzle 180 is desirably sized to pass through the cannula instrument 184. For material strength, the nozzle 180 can be formed from a substantially rigid metal material, e.g., stainless steel or a high strength plastic.

The stylet 182 includes a handle 192, which rests on the proximal connector 186 of the nozzle when the stylet 182 is fully inserted into the nozzle 180. When the handle is rested, the distal ends of the stylet 182 and nozzle 180 align. The presence of the stylet 182 inside the nozzle 180 desirably closes the interior bore.

In use, the nozzle 180 can be coupled to the syringe 104 and inserted through the cannula instrument 184 into a material-receiving cavity (not shown) formed within a bone. Material 62 in the syringe 104 is injected into the nozzle 180 where it desirably passes into the bone. When a sufficient amount of material 62 is injected into the bone and/or nozzle 180, the syringe 104 may be removed from the nozzle 180.

The stylet 182 can then be inserted into the nozzle 180, and advanced through the nozzle, desirably pressurizing the material 62 and pushing it out of the nozzle 180. In one disclosed embodiment, the stylet 182 has a diameter of approximately 0.118 in. The cross-sectional area of this stylet 182 is approximately 0.010936 in2, and the nozzle 180 desirably contains approximately 1.5 cc of filler material. In this embodiment, pushing the stylet 182 into the nozzle 180 with a force of force of ten (10) pounds can produce a pressure of approximately 914 lb-in2 in the filler material 62 within the nozzle 180. In an alternate embodiment, the stylet 182 has a diameter of approximately 0.136 in. A force of ten (10) pounds utilized on this stylet can produce a pressure of approximately 688 lb-in2 in the filler material 62 within the nozzle 180.

The nozzle 180 and stylet 182 can be used in a similar manner as a combination ram 183 to push the filler material 62 through the cannula instrument 184 into the bone. For example, where filler material 62 is within the cannula instrument 184, the insertion of the ram 183 into the cannula 184 will desirably displace the material 62, forcing the material 62 from the distal end of the cannula 184 into the bone. In one embodiment, the diameter of the ram 183 is approximately 0.143 in. In this embodiment, pushing the ram 183 with a force of ten (10) pounds is capable of producing a pressure of 622 lb-in2 in the filler material 62 within the cannula 184. As the ram 183 advances through the cannula 184, it will desirably displace the filler material 62 in the cannula 184. The ram 183, therefore, acts as a positive displacement "piston" or "pump," which permits the physician to accurately gauge the precise amount of filler material 62 that is injected into the bone.

If the filler material is very viscous, this material will typically strongly resist being pumped through a delivery system. Generally, the greater distance the filler material must travel through the system, the greater the pressure losses will be from such factors as viscosity of the material and frictional losses with the walls. In order to account for these losses, existing delivery systems typically highly pressurize the filler material, often to many thousands of pounds of pressure. Not only does this require stronger pumps and reinforced fittings for the delivery system, but such systems often cannot dispense filler material in very precise amounts. Moreover, if the filler material hardens over time, the system must produce even greater pressures to overcome the increased flow resistance of the material.

The disclosed systems and methods obviate and/or reduce the need for complex, high pressure injection systems for delivery of filler materials because the disclosed ram 183 travels subcutaneously through the cannula 184, and displaces filler material 62 out the distal end of the cannula 184, the amount of filler material being pushed by the ram 183 (and the total amount of filler material 62 within the cannula 184) progressively decreases as filler material is injected into the bone. This desirably results in an overall decrease in resistance to movement of the ram during injection. Moreover, because the amount of material being "pushed" by the ram 183 decreases, an increase in the flow resistance of the curing filler material does not necessarily require an increase in injection pressure. In addition, because the ram 183 travels within the cannula 184, and can travel percutaneously to the injection site, the filler material need only be "pumped" a short length before it exits the cannula and enters the bone, further reducing the need for extremely high pressures. If injection of additional filler material is required, the ram can be withdrawn from the cannula, additional, filler material can be introduced into the cannula, and the process repeated. Thus, the present arrangement facilitates injection of even extremely viscous materials under well controlled conditions. Moreover, by utilizing varying diameters of cannulas, nozzles and stylets in this manner, a wide range of pressures can be generated in the filler material 62. If desired, the disclosed devices could similarly be used to inject filler material through a spinal needle assembly directly into bone, in a vertebroplasty-like procedure, or can be used to fill a cavity created within the bone.

If desired, after the physician has filled the cavity with material 62, the physician may choose to continue injecting additional material 62 into the vertebral body. Depending upon the local conditions within the bone, this additional material may merely increase the volume of the cavity (by further compacting cancellous bone), or may travel into the compressed and/or uncompressed cancellous bone surrounding the cavity, which may serve to further compress cancellous bone and/or further enhance the compressive strength of the vertebral body.

When the physician is satisfied that the material 62 has been amply distributed inside the cavity portion, the physician withdraws the tamping instrument 124 from the cannula instrument 84. The physician preferably first twists the tamping instrument 124 to cleanly break contact with the material 62.

Once all cavity portions have been filled and tamped in the above described manner, the cannula instruments 84 can be withdrawn and the incision sites sutured closed. The bilateral bone treatment procedure is concluded.

Eventually the material 62, if cement, will harden to a rigid state within the cavities 64. The capability of the vertebral bodies 26A, 26B, and 26C to withstand loads has thereby been improved.

FIGS. 9B through 9D depict an alternate method of filling a cavity 60 formed within a vertebral body. In this embodiment, a cannula instrument 84 has been advanced through a pedicle 42 of the vertebral body by, providing access to a cavity 60 formed therein. A nozzle 180 is advanced into the vertebral body, with the distal tip of the nozzle 180 desirably positioned near the anterior side of the cavity 60. Filler material 62 is slowly injected through the nozzle 180 into the cavity 60. As injection of filler material 62 continues, the nozzle 180 is withdrawn towards the center of the cavity 60. See FIG. 9c. Desirably, as the nozzle 180 is withdrawn, the distal tip of the nozzle 180 will remain substantially in contact with the growing bolus of filler material 62. Once the nozzle 180 is positioned near the center of the cavity 60, additional filler material 62 is injected through the nozzle 180 to substantially fill the cavity 60. The nozzle is then removed from the cavity 60.

Figure 33:
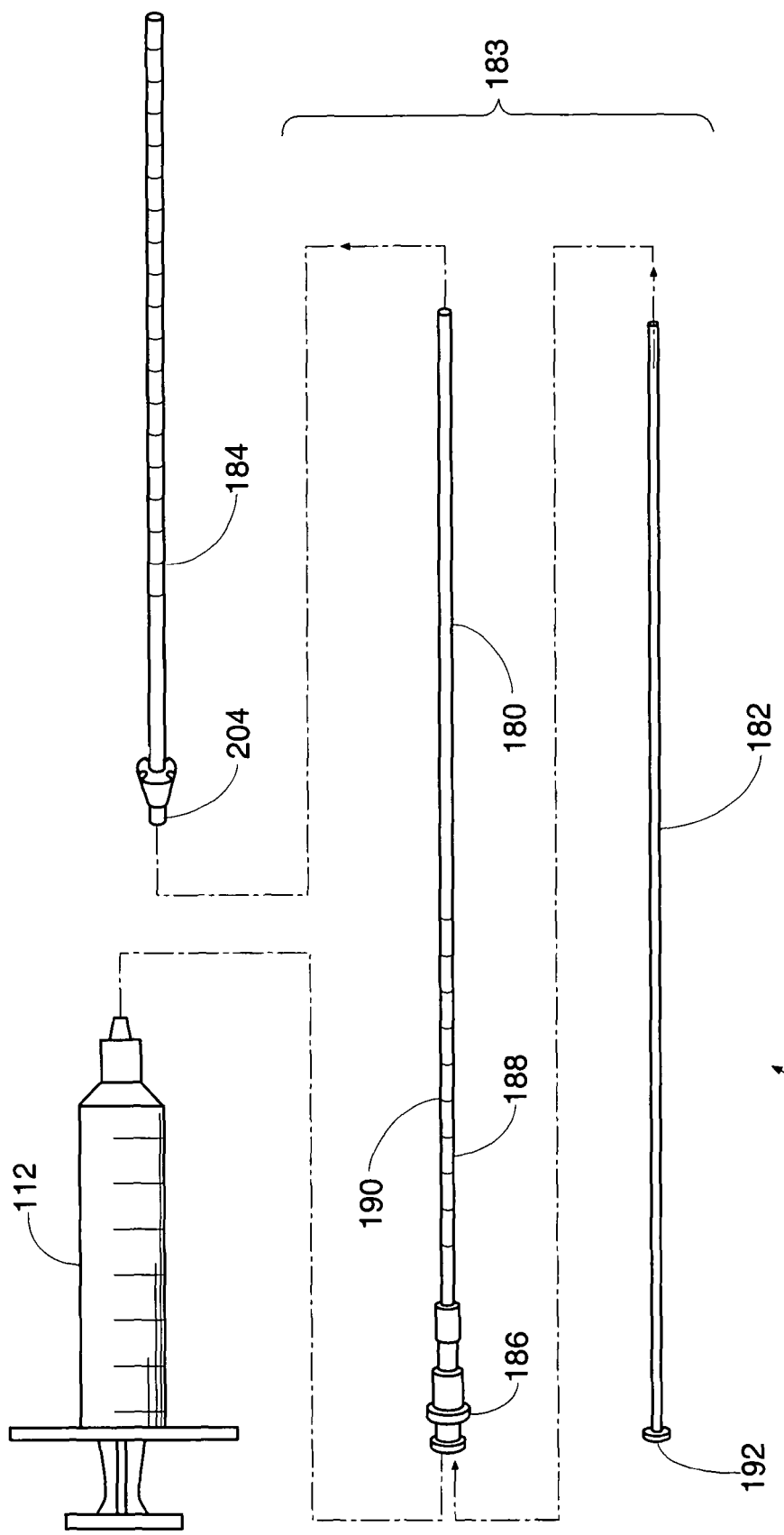
FIG. 33 is an exploded perspective view of a cannula and material introducing device, which embodies features of the invention.

If desired, the nozzle can be attached to a syringe 104 (see FIG. 33) containing filler material. In one embodiment, the syringe 104 will contain an amount of filler material equal to the volume of the cavity 60 formed within the vertebral body, with the nozzle containing an additional 1.5 cc of filler material. In this embodiment, the cavity 60 will initially be filled with filler material expelled from the syringe 104. Once exhausted, the syringe 104 can be removed from the nozzle 180, a stylet 182 inserted into the nozzle 180, and the remaining filler material within the nozzle 180 pushed by the stylet 182 into the vertebral body. Desirably, the additional filler material from the nozzle 180 will extravazate into the cancellous bone, compress additional cancellous bone and/or slightly increase the size of the cavity 60.

The disclosed method desirably ensures that the cavity is completely filled with filler material. Because the patient is often positioned front side (anterior side) down during the disclosed procedures, the anterior section of the cavity is often the lowest point of the cavity. By initially filling the anterior section of the cavity with filler material, and then filling towards the posterior side of the cavity, fluids and/or suspended solids within the cavity are desirably displaced by the filler material and directed towards the posterior section of the cavity, where they can exit out the cannula. In this manner, "trapping" of fluids within the cavity and/or filler material is avoided and a complete and adequate fill of the vertebral body is ensured.

If desired, the filler material can be allowed to harden and/or cure before injection into the vertebral body. For example, in one embodiment, the filler material comprises bone cement, which is allowed to cure to a glue or putty-like state before being injected into the cavity. In this embodiment, the cement would desirably have a consistency similar to toothpaste as the cement begins to extrude from the nozzle.

The selected material 62 can also be an autograft or allograft bone graft tissue collected in conventional ways, e.g., in paste form (see Dick, "Use of the Acetabular Reamer to Harvest Autogenic Bone Graft Material: A Simple Method for Producing Bone Paste," Archives of Orthopaedic and Traumatic Surgery (1986), 105: 235-238), or in pellet form (see Bhan et al, "Percutaneous Bone Grafting for Nonunion and Delayed Union of Fractures of the Tibial Shaft," International Orthopaedics (SICOT) (1993) 17: 310-312). Alternatively, the bone graft tissue can be obtained using a Bone Graft Harvester, which is commercially available from SpineTech. Using a funnel, the paste or pellet graft tissue material is loaded into the cannula instrument 84 30. The tamping instrument 124 is then advanced into the cannula instrument 84 in the manner previously described, to displace the paste or pellet graft tissue material out of the cannula instrument 84 and into the cavity portion.

The selected material 62 can also comprise a granular bone material harvested from coral, e.g., ProOsteon™ calcium carbonate granules, available from Interpore. The granules are loaded into the cannula instrument 84 using a funnel and advanced into the cavity using the tamping instrument 124.

The selected material 62 can also comprise demineralized bone matrix suspended in glycerol (e.g., Grafton™ allograft material available from Osteotech), or SRS™ calcium phosphate cement available from Novian. These viscous materials, like the bone cement previously described, can be loaded into the syringe 112 and injected into the cavity using the nozzle 114, which is inserted through the cannula instrument 84 into the cavity portion. The tamping instrument 124 is used to displace residual material from the cannula instrument 84 into the cavity portion, as before described.

The selected material 62 can also be in sheet form, e.g. Collagraf™ material made from calcium carbonate powder and collagen from bovine bone. The sheet can be rolled into a tube and loaded by hand into the cannula instrument 84. The tamping instrument 124 is then advanced through the cannula instrument 84, to push and compact the material in the cavity portion.

Figure 23:
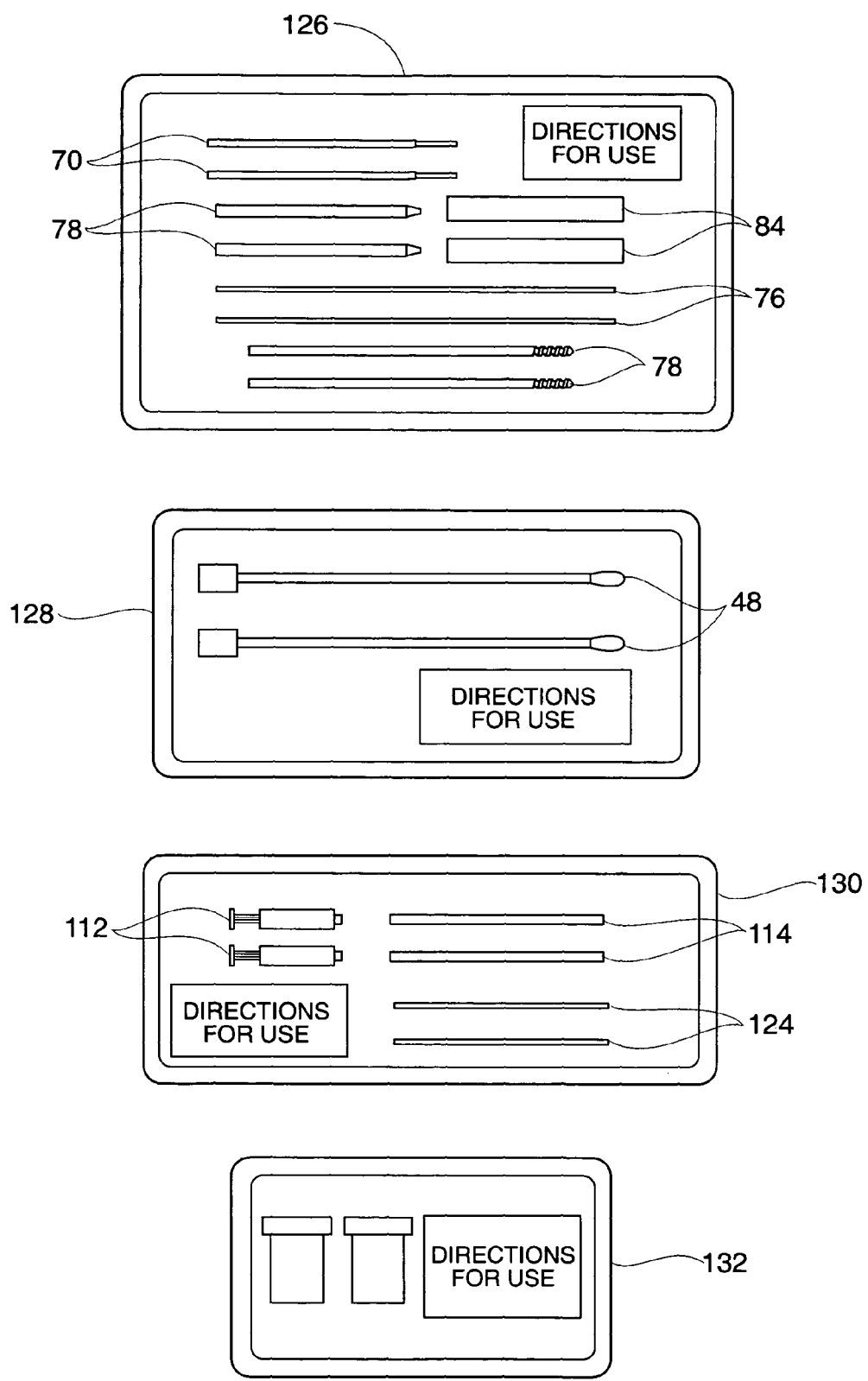
FIG. 23 are top views of kits which hold, prior to use, the various instruments and tools usable to create multiple access paths in a single vertebral body, to compact cancellous bone and form a cavity to be filled with a material, as generally shown in FIGS. 16A to 16I.

The various instruments just described to carry out a bilateral procedure can be arranged in one or more prepackage kits 126, 128, and 130, as FIG. 23 shows. For example, a first kit 126 can package an access instrument group for achieving bilateral access into a single vertebral body (comprising, e.g., at least one spinal needle instrument 70, at least one guide wire instrument 76, at least one obturator instrument 78, two cannula instruments 84, and at least one drill bit instrument 88). Alternatively, the first kit 126 can contain at least one trocar 330 and two cannula instruments 84, which together form two composite instruments 310.

A second kit 128 can package a cavity forming instrument group for the bilateral access (comprising, e.g., two cavity forming tools 48). A third kit 130 can package a material introduction instrument group for the bilateral access (comprising, e.g., at least one syringe 112, at least one nozzle 114, and at least one tamping instrument 124). Alternatively, the kit 130 can comprise a material introduction instrument group comprising a syringe 112, a cannula 84 and a tamping instrument 124 sized to fit within the cannula. The kits 126, 128, and 130 also preferably include directions for using the contents of the kits to carry out a desired bilateral procedure, as above described.

A fourth kit 132 can also be included, to include the ingredients for the filling material 62, which, as before explained, may contain a predetermined amount of a radiopaque material, e.g., barium or tungsten, sufficient to enable visualization of the flow of material 62 into the cavity portion. The kit 132 also preferably include directions for mixing the material 62 to carry out a desired bilateral procedure, as above described.

Of course, it should be understood that the individual instruments could be kitted and/or sold individually, with instructions on their use. If desired, individual instrument kits could be combined to form procedure kits tailored to individual procedures and/or physician preference. For example, a general instrument kit for performing a single level procedure could comprise a guide wire instrument 76, an obturator instrument 78, a cannula instrument 84, and a drill bit instrument 88.

D. Alternative Cavity Formation and Filling Techniques

A cavity, filled with a compression-resistant material, can be created within a vertebral body in alternative ways.

For example (see FIG. 24A), a small diameter expandable body 150 can be introduced into a vertebral body through the stylus 72 of a spinal needle assembly 70, or another needle sized approximately 8 to 11 gauge. Expanding the small structure 150 compacts cancellous bone to form a desired cement flowpath within the vertebral body and/or a barrier region 152 substantially surrounding the structure 150. Alternatively, a mechanical tamp, reamer, or single or multiple hole puncher can be used to create a desired cement flowpath within the vertebral body and/or compact cancellous bone to form a small barrier region 152. The desired cement flowpath and/or compacted cancellous bone surrounding the barrier region 152 will reduce and/or prevent extravazation of the flowable material injected outside the vertebral body.

A flowable filling material 154, e.g., bone cement, can be pumped under high pressure by a pump 156 through the needle 72 into the desired cement flowpath and/or barrier region 152 (see FIG. 24B) in a volume that exceeds the volume of the flowpath/barrier region 152. The filling material 154 pushes under pressure against the compacted cancellous bone, enlarging the volume of the flowpath/barrier region 152 as material 154 fills the flowpath/region 152 (see FIG. 24C). The interior pressure exerted by the filling material can also serve to move recently fractured cortical bone back toward its pre-fracture position. The flowable material is allowed to set to a hardened condition, as previously explained.

Figure 12:
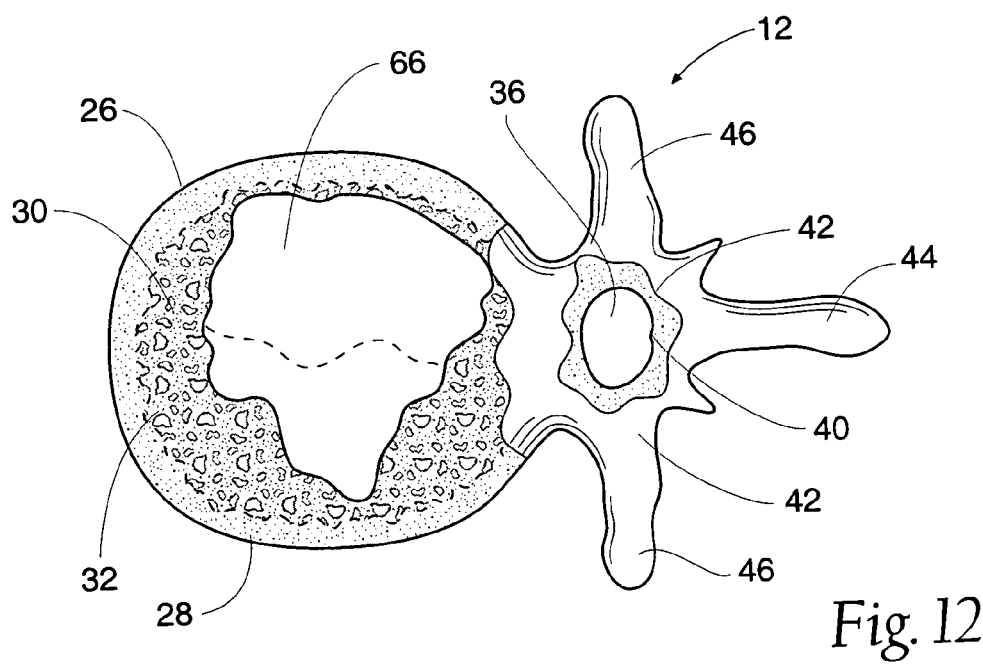
FIG. 12 is a coronal view of the vertebral body shown in FIG. 10, with the tools removed after formation of generally asymmetric cavities.
Figure 24A:
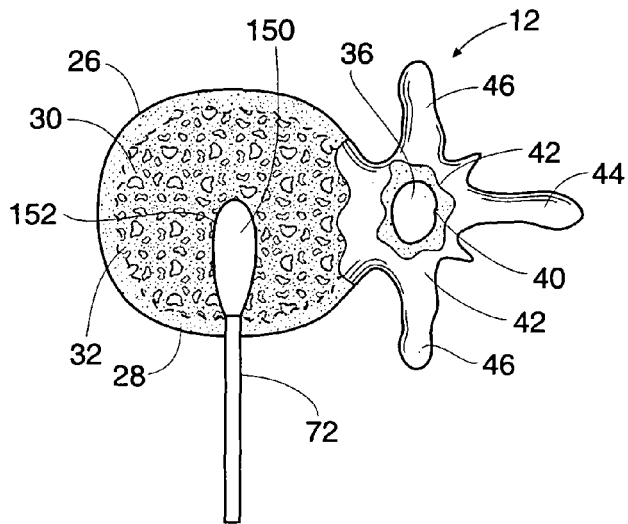
FIGS. 24A to 24C are coronal views of a vertebral body, showing a small expandable body deployed through a needle to create a small cavity, and the injection of a filling material under pressure through the needle to fill and enlarge the cavity to strengthen the vertebral body.
Figure 24B:
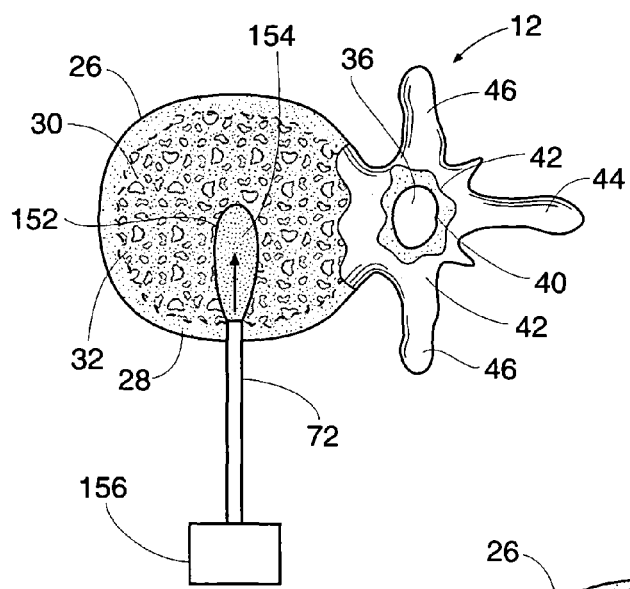
Figure 24C:
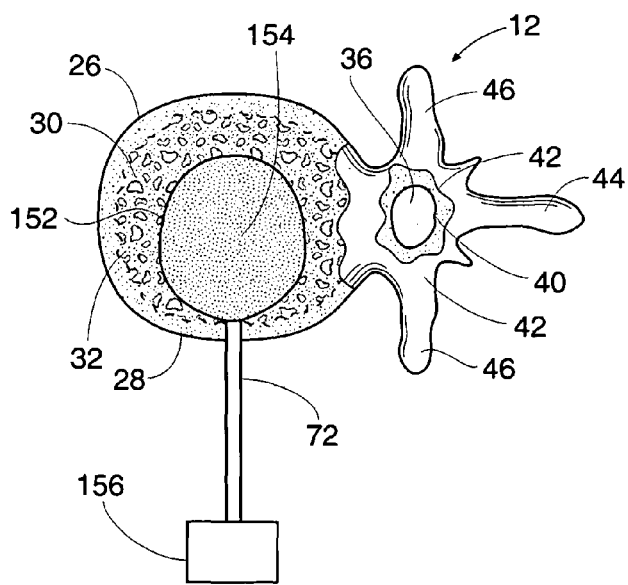

A multiple level procedure can be performed using different treatment techniques on different vertebral body levels. For example, if a given vertebral body layer has developed cracks and experienced compression fracture, the cavity-forming and bone lifting techniques previously described can be advantageously used. The cavity forming and bone lifting technique can comprise use of one or more expandable larger bodies 56 followed by low pressure introduction of filling material (as shown in FIGS. 10 to 12), or use of one or more smaller expandable bodies 150 followed by high pressure introduction of filling material (as shown in FIGS. 24A to 24C), or use of a combination thereof (e.g., in a bilateral procedure).

It may be indicated to treat another vertebral body utilizing vertebroplasty techniques, which have as their objectives the strengthening of the vertebral body and the reduction of pain. For example, where the end plates of the vertebral body have depressed to a point where an expandable structure cannot be safely inserted and/or expanded within the vertebral body, bone cement can be injected under pressure through a needle directly into the cancellous bone of the vertebral body (without cavity formation). The bone cement penetrates cancellous bone. To reduce flow resistance to the cement, the needle can possess an increasing interior diameter, as shown in FIG. 22A, 22B, or 22C. The reduced flow resistance makes possible the use of more viscous cement, to thereby reduce the possibility that the cement will exude from the vertebral body.

Different treatment techniques can also be used in different regions of the same vertebral body. For example, any of the above described cavity-forming and bone lifting techniques can be applied in one region of a vertebral body, while conventional vertebroplasty can be applied to another region of the same vertebral body. Such a procedure would be especially well suited for treatment of scoliosis, as previously discussed herein. Alternatively, the various disclosed techniques can be utilized in separate vertebral bodies within the same spinal column.

The features of the invention are set forth in the following claims.

We claim:

1. A system for treating a vertebral body comprising
a cannula sized and configured to establish a percutaneous path leading into a vertebral body;
a cavity creating device comprising
a shaft having an outer surface and a distal end portion sized to extend through the cannula and into the vertebral body,
an expandable body having a proximal region attached to the outer surface of the distal end portion of the shaft and having a distal region positioned distally beyond the distal end portion of the shaft, the expandable body sized and configured for contacting cancellous bone and for undergoing expansion between a collapsed condition and an expanded condition to form a cavity in cancellous bone of the vertebral body, and
a tubular fluid transport member extending through the shaft and beyond the distal end portion of the shaft and extending through the expandable body, the tubular fluid transport member sized and configured to convey fluid through the distal region of the expandable body and into the cavity;
a device coupled to the shaft to expand the expandable body from the collapsed condition to the expanded condition and to return the expandable body from the expanded condition to the collapsed condition;
a source of fluid coupled to the tubular fluid transport member to convey fluid through the distal region of the expandable body and into the cavity to resist formation of a vacuum within the cavity as the expandable body is returned from the expanded condition to the collapsed condition; and
a device to convey a filling material into the cavity.

2. A system according to claim 1
wherein the expandable body, during expansion to the expanded condition, applies force capable of moving cortical bone toward a restored position, and
wherein fluid conveyed through the distal end portion of the shaft into the cavity resists movement of cortical bone away from the restored position as the expandable body is returned from the expanded condition to the collapsed condition.

3. A system according to claim 1
wherein the source of fluid comprises a source of liquid.

4. A system according to claim 1
wherein the source of fluid comprises a source of air.

5. A system according to claim 1
wherein the source of fluid includes a pump.

6. A system according to claim 1
further including a source of compression-resistant material comprising the filling material.

7. A system according to claim 1
further including a source of a medication comprising the filling material.

8. A system according to claim 1
further including a source of a flowable material which sets to a hardened condition comprising the filling material.

9. The system of claim 1 wherein the tubular fluid transport member extends beyond the distal region of the expandable body.

* * * * *